(12) United States Patent
Modliszewski et al.

(10) Patent No.: US 7,807,194 B2
(45) Date of Patent: Oct. 5, 2010

(54) HOMOGENEOUS, THERMOREVERSIBLE GEL FILM CONTAINING KAPPA-2 CARRAGEENAN AND SOFT CAPSULES MADE THEREFROM

(75) Inventors: James J. Modliszewski, Brick, NJ (US); Arthur D. Ballard, Westport, ME (US); Christopher J. Sewall, Hope, ME (US); William R. Blakemore, Topsham, ME (US); Peter J. Riley, Yardley, PA (US)

(73) Assignee: FMC Corporation, Philadelphia, PA (US)

( * ) Notice: Subject to any disclaimer, the term of this patent is extended or adjusted under 35 U.S.C. 154(b) by 1407 days.

(21) Appl. No.: 10/824,860

(22) Filed: Apr. 14, 2004

(65) Prior Publication Data

US 2005/0019374 A1 Jan. 27, 2005

Related U.S. Application Data

(60) Provisional application No. 60/462,785, filed on Apr. 14, 2003, provisional application No. 60/462,617, filed on Apr. 14, 2003, provisional application No. 60/462,783, filed on Apr. 14, 2003, provisional application No. 60/462,794, filed on Apr. 14, 2003, provisional application No. 60/462,792, filed on Apr. 14, 2003, provisional application No. 60/462,793, filed on Apr. 14, 2003, provisional application No. 60/462,758, filed on Apr. 14, 2003, provisional application No. 60/462,721, filed on Apr. 14, 2003.

(51) Int. Cl.
*A61K 9/14* (2006.01)
*A61K 9/16* (2006.01)
*A61K 9/20* (2006.01)
*A61K 9/28* (2006.01)
*A61K 9/30* (2006.01)
*A61K 9/36* (2006.01)
*A61K 9/48* (2006.01)
*C08L 3/02* (2006.01)
*C08L 5/00* (2006.01)
*C09D 103/02* (2006.01)
*C09D 105/00* (2006.01)
*C09J 130/02* (2006.01)

(52) U.S. Cl. .............. 424/451; 106/205.01; 106/205.9; 424/463; 424/464; 424/474; 424/479; 424/489; 424/490; 424/493; 424/496; 524/55

(58) Field of Classification Search .................. None
See application file for complete search history.

(56) References Cited

U.S. PATENT DOCUMENTS

| | | |
|---|---|---|
| 348,669 A | 9/1886 | Gruber |
| 2,802,000 A | 8/1957 | Caldwell et al. |
| 2,813,093 A | 11/1957 | Caldwell et al. |
| 2,825,727 A | 3/1958 | Caldwell |
| 2,876,217 A | 3/1959 | Paschall |
| 3,058,827 A | 10/1962 | Graham |
| 3,094,517 A | 6/1963 | Stanley |
| 3,176,003 A | 3/1965 | Stancioff |
| 3,329,509 A | 7/1967 | Julius |
| 3,378,546 A | 4/1968 | Tsuzuki |
| 3,460,717 A | 8/1969 | Thomas |
| 3,499,962 A | 3/1970 | Warzburg et al. |
| 3,505,110 A | 4/1970 | Kesler et al. |
| 3,607,394 A | 9/1971 | Germino et al. |
| 3,865,603 A | 2/1975 | Szymanski et al. |
| 3,956,173 A | 5/1976 | Towle |
| 3,962,482 A | 6/1976 | Comer et al. |
| 4,009,291 A | 2/1977 | Mitchell et al. |
| 4,026,986 A | 5/1977 | Christen et al. |
| 4,096,327 A | 6/1978 | Guiseley |
| 4,129,134 A | 12/1978 | Hind et al. |
| 4,231,803 A | 11/1980 | Bovier et al. |
| 4,276,320 A | 6/1981 | Moirano |
| 4,443,486 A | 4/1984 | Guiseley |
| 4,600,439 A | 7/1986 | Schneider et al. |
| 4,615,897 A | 10/1986 | Brown et al. |
| 4,626,288 A | 12/1986 | Trzasko et al. |
| 4,632,848 A | 12/1986 | Gosset et al. |
| 4,643,894 A | 2/1987 | Porter et al. |
| 4,725,441 A | 2/1988 | Porter |
| 4,738,724 A | 4/1988 | Wittwer et al. |
| 4,795,642 A | 1/1989 | Cohen et al. |
| 4,808,707 A | 2/1989 | Daly et al. |
| 4,828,841 A | 5/1989 | Porter |
| 4,851,394 A | 7/1989 | Kubodera |
| 4,935,243 A | 6/1990 | Borkan et al. |
| 5,002,934 A | 3/1991 | Norton et al. |
| 5,051,304 A | 9/1991 | David et al. |
| 5,089,307 A | 2/1992 | Ninomiya et al. |
| 5,146,730 A | 9/1992 | Sadek et al. |
| 5,224,989 A | 7/1993 | Likarova |
| 5,264,223 A | 11/1993 | Yamamoto et al. |

(Continued)

FOREIGN PATENT DOCUMENTS

EP 0 169 319 1/1986

(Continued)

OTHER PUBLICATIONS

Painter et al. Fundamentals of Polymer Science. Lancaster: Technomic Publishing 1994 p. 15.*

(Continued)

*Primary Examiner*—Robert A Wax
*Assistant Examiner*—Caralynne Helm

(57) ABSTRACT

The present invention is directed to a homogeneous, thermoreversible gel film comprising a film forming amount of kappa-2 carrageenan, and optionally at least one of a plasticizer, a second film former, a bulking agent, and a pH controlling agent; and processes for the preparation thereof. The present invention is also directed to soft capsules and solid forms containing the gel film, as well as processes for the preparation thereof.

42 Claims, 5 Drawing Sheets

U.S. PATENT DOCUMENTS

| | | | |
|---|---|---|---|
| 5,334,640 | A | 8/1994 | Desai et al. |
| 5,342,626 | A | 8/1994 | Winston, Jr. et al. |
| 5,422,134 | A | 6/1995 | Hart et al. |
| 5,431,917 | A | 7/1995 | Yamamoto et al. |
| 5,451,673 | A | 9/1995 | Fishman et al. |
| 5,484,598 | A | 1/1996 | Schurig et al. |
| 5,525,368 | A | 6/1996 | Rha et al. |
| 5,549,983 | A | 8/1996 | Yamanis |
| 5,550,178 | A | 8/1996 | Desai et al. |
| 5,554,385 | A | 9/1996 | Stroud |
| 5,569,466 | A | 10/1996 | Tanner et al. |
| 5,587,412 | A | 12/1996 | Borchers et al. |
| 5,614,217 | A | 3/1997 | Chiprich et al. |
| 5,620,757 | A | 4/1997 | Ninomiya et al. |
| 5,646,206 | A | 7/1997 | Coffin et al. |
| 5,656,294 | A | 8/1997 | Friend et al. |
| 5,672,699 | A | 9/1997 | Billmers et al. |
| 5,726,008 | A | 3/1998 | Maskasky |
| 5,756,123 | A | 5/1998 | Yamamoto et al. |
| 5,804,243 | A | 9/1998 | Loh et al. |
| 5,811,388 | A | 9/1998 | Friend et al. |
| 5,817,323 | A | 10/1998 | Hutchinson et al. |
| 5,820,259 | A | 10/1998 | Cummins et al. |
| 5,932,639 | A | 8/1999 | Eden et al. |
| 5,942,266 | A | 8/1999 | Okamura et al. |
| 5,948,430 | A | 9/1999 | Zerbe et al. |
| 5,976,586 | A | 11/1999 | Feller |
| 6,030,641 | A | 2/2000 | Yamashita et al. |
| 6,063,915 | A | 5/2000 | Hansen et al. |
| 6,066,368 | A | 5/2000 | Billmers et al. |
| 6,099,876 | A | 8/2000 | Nussinovitch |
| 6,143,324 | A | 11/2000 | Michaud et al. |
| 6,146,570 | A | 11/2000 | Stern |
| 6,210,709 | B1 | 4/2001 | Laba et al. |
| 6,214,376 | B1 | 4/2001 | Gennadios |
| 6,326,028 | B1 | 12/2001 | Nivaggioli et al. |
| 6,331,205 | B1 | 12/2001 | Paris |
| 6,340,473 | B1 | 1/2002 | Tanner et al. |
| 6,352,719 | B1 | 3/2002 | Brown et al. |
| 6,375,981 | B1 | 4/2002 | Gilleland et al. |
| 6,387,354 | B1 | 5/2002 | Bixler et al. |
| 6,432,448 | B1* | 8/2002 | Augello et al. ............... 424/479 |
| 6,447,755 | B1 | 9/2002 | Ballard |
| 6,479,649 | B1 | 11/2002 | Tsai et al. |
| 6,497,887 | B1 | 12/2002 | Zecchino et al. |
| 6,517,865 | B2 | 2/2003 | Cade et al. |
| 6,528,088 | B1 | 3/2003 | Gilleland et al. |
| 6,582,727 | B2 | 6/2003 | Tanner et al. |
| 6,607,748 | B1 | 8/2003 | Lenaerts et al. |
| 6,635,275 | B1 | 10/2003 | Scott et al. |
| 6,649,188 | B2 | 11/2003 | Gilleland et al. |
| 6,790,495 | B1 | 9/2004 | Tomka et al. |
| 6,949,256 | B2* | 9/2005 | Fonkwe et al. ............... 424/451 |
| 6,967,037 | B1 | 11/2005 | Jonsson et al. |
| 2002/0026771 | A1 | 3/2002 | Brown |
| 2002/0081331 | A1 | 6/2002 | Tanner et al. |
| 2002/0122822 | A1 | 9/2002 | Bunick et al. |
| 2002/0142031 | A1 | 10/2002 | Gilleland et al. |
| 2002/0176317 | A1 | 11/2002 | Bellasalma et al. |
| 2003/0084641 | A1 | 5/2003 | Tanner et al. |
| 2003/0085487 | A1 | 5/2003 | Tanner et al. |
| 2003/0138482 | A1 | 7/2003 | Fonkwe et al. |
| 2003/0211146 | A1 | 11/2003 | Scott et al. |
| 2004/0013723 | A1* | 1/2004 | Parikh et al. ................. 424/456 |
| 2004/0052839 | A1 | 3/2004 | Archibald et al. |
| 2004/0087669 | A1 | 5/2004 | Hausmanns et al. |
| 2004/0180083 | A1 | 9/2004 | Shiraishi |
| 2004/0192907 | A1 | 9/2004 | Resch et al. |
| 2005/0008677 | A1* | 1/2005 | Modliszewski et al. ..... 424/439 |
| 2005/0013847 | A1* | 1/2005 | Ballard et al. ................ 424/439 |
| 2005/0014852 | A1* | 1/2005 | Sewall et al. .................. 516/99 |
| 2005/0019294 | A1* | 1/2005 | Modliszewski et al. .. 424/70.13 |
| 2005/0019295 | A1* | 1/2005 | Ballard et al. ............ 424/70.13 |
| 2005/0037064 | A1 | 2/2005 | Basquin et al. |
| 2005/0048185 | A1* | 3/2005 | Ballard et al. ................ 426/573 |
| 2005/0069579 | A1 | 3/2005 | Kamaguchi et al. |
| 2005/0070703 | A1 | 3/2005 | Muller et al. |
| 2005/0089548 | A1 | 4/2005 | Virgalitto et al. |
| 2005/0106233 | A1 | 5/2005 | Andersen et al. |
| 2005/0163833 | A1 | 7/2005 | Muller |

FOREIGN PATENT DOCUMENTS

| | | |
|---|---|---|
| EP | 0 400 484 | 12/1990 |
| EP | 0 408 503 | 1/1991 |
| EP | 0 409 781 | 1/1991 |
| EP | 0 409 782 | 1/1991 |
| EP | 0 409 788 | 1/1991 |
| EP | 0 471 558 | 2/1992 |
| EP | 0 547 551 | 6/1993 |
| EP | 0 606 486 | 7/1994 |
| EP | 0 622 408 | 11/1994 |
| EP | 0 633 896 | 1/1995 |
| EP | 0 714 656 A1 | 6/1996 |
| EP | 0 761 691 | 3/1997 |
| EP | 1297827 A2 | 4/2003 |
| JP | 60055039 A1 | 3/1985 |
| JP | 60088047 A | 5/1985 |
| JP | 61 10508 A | 1/1986 |
| JP | 62-186754 | 8/1987 |
| JP | 63-164858 | 7/1988 |
| JP | 3-12231 | 1/1991 |
| JP | 3-53873 | 3/1991 |
| JP | 09-25228 | 1/1997 |
| JP | 2000125801 A | 5/2000 |
| JP | 2001-39863 | 2/2001 |
| JP | 2003-504326 | 2/2003 |
| JP | 2003-299714 | 10/2003 |
| JP | 2004-167084 | 6/2004 |
| JP | 2005-513255 | 5/2005 |
| RU | 352444 A | 10/1972 |
| WO | WO 94/25493 | 11/1994 |
| WO | WO 97/49762 | 12/1997 |
| WO | WO 98/20860 | 5/1998 |
| WO | WO 99/07347 | 2/1999 |
| WO | WO 00/10538 | 3/2000 |
| WO | WO 00/18835 | 4/2000 |
| WO | WO 00/36930 | 6/2000 |
| WO | WO-01/03677 | 1/2001 |
| WO | WO 01/37817 | 5/2001 |
| WO | WO 01/91721 | 12/2001 |
| WO | WO 01/92400 | 12/2001 |
| WO | WO 01/92401 | 12/2001 |
| WO | WO 02/43657 A2 | 6/2002 |
| WO | WO 03/009832 | 2/2003 |
| WO | WO-03/035044 | 5/2003 |

OTHER PUBLICATIONS

JP01-143827—English Abstract (Micropatent) and partial English translation.

JP05-43471—English Abstract (Micropatent) and partial English translation.

JP09-25228—English Abstract (Micropatent) and partial English translation.

JP2001-39863—English Abstract (Micropatent) and partial English translation.

JP2003-299714—English Abstract (Micropatent) and partial English translation.

JP2004-167084—English Abstract (Micropatent) and partial English translation.

JP2005-112849—partial English translation.

JP2005-508359—partial English translation.

FMC Technical Bulletin, "NJAI. 798 Cell Immobilization Carrageenan", 6 pages.

FMC Corporation Marine Colloids Division Application Bulletin G-39 "Water-Gelling Properties of Carrageenan" p. 1 to p. 16, Jun. 1990.

de Vries J., "Interaction of carrageenan with other ingredients in dairy dessert gels", Gums and stabilisers for the food industry 11: proceedings of the 11th conference, Wrexham, vol. 11 (2002), No. -, pp. 201-210, Jul. 2001.

R. Falshaw et al., "Structure and performance of commercial K-2 carrageenan extracts", Food Hydrocolloids, vol. 17, pp. 129-139, 2003.

FMC BioPolymer, "Carrageenan Matrices for Entrapment", Issue No. 1, Apr. 1993.

Henry J. Witt, "Carrageenan Nature's Most Versatile Hydrocolloid", pp. 347-360, 1985.

Glicksman, M., "Gum Technology in the Food Industry", Academic Press, pp. 213-228, 1969.

C. J. Lawson et al., "Carrageenans", J.C.S. Perkin I, pp. 2177-2182, 1973.

H. J. Bixler, "Recent developments in manufacturing and marketing carrageenan", Hydrobiologia, pp. 35-57, 1996.

M. C. Matulewicz et al., "Carrageenan Systems from Tetrasporic or Cystocarpic Stages of Gigartina Skottsbergii", Phytochemistry, vol. 28, pp. 2937-2941, 1989.

M. C. Matulewicz et al., "Methylation Analysis of Carrageenans from Tetrasporic and Cystocarpic Stages of Gigartina Skottsbergii", Phytochemistry, vol. 29, No. 11, pp. 3407-3410, 1990.

C. Rochas et al., "Relation Between the Molecular Strcture and Mechanical Properties of Carrageenan Gels", Carbohydrate Polymers, vol. 10, pp. 115-127, 1989.

Stancioff, D. J. and Stanley, N. F., "Infrared and Chemical Studies on Algal Polysaccharides", Prod. Intl. Seaweed Symp. 6, pp. 595-609, 1969.

Bellion, C. et al, Analysis of Kappa-Iota Hybrid Carrageenans with Kappa-Carrageenase, Iota-Carrageenase and $^{13}$C N.M.R., Xth International Seaweed Symposium, Walter de Gruyter & Co., Berlin-New York, pp. 379-384, 1981.

Peats, S., "The Infrared Spectra of Carrageenans Extracted from Various Algae", Xth International Seaweed Symposium, Walter de Gruyter & Co., Berlin-New York, pp. 495-502, 1981.

JP 5-4914 English language Abstract (espace.net), 1993.

JP 7-196478 English language Abstract (European Patent Office), 1995.

"Water Gelling Applications of Carrageenan," FMC Corporation, Springfield, NJ, ((1981).

F. Sedlmeyer, et al., "Influence of the composition of milk-protein κ/ι-hybrid-carrageenan gels on product properties," Colloids and Surfaces B: Biointerfaces, (2003), vol. 31, pp. 13-20.

Eleya, et al., "Rheology of κ-carrageenan and B-lactoglobulin mixed gels", Food Hydrocolloids, vol. 14, pp. 29-40, 2000.

Falshaw et al., "Structure and performance of commercial kappa-2 carrageenan extracts I. Structure analysis",, Food Hydrocolloids, vol. 15, pp. 441-452; 2001.

Villanueva et al., "Structure and functional performance of gigartinacean kappa-iota hydrid carrageenan and solieriacean kappa-iota carrageenan blends", Food Hydrocolloids. vol. 18, pp. 283-292; 2004.

Bixler et al., "Kappa-2 carrageenan: structure and performance of commercial extracts II. Performance in two simulated dairy application", Food Hydrocolloids, vol. 15, pp. 619-630; 2001.

van de Velde et al., "On the structure of κ/ι-hybrid carrageenans", Carbohydrate Research, vol. 331, pp. 271-283, 2001.

C. Rochas et al., "Role of the Molecular Weight on the Mechanial Properties of Kappa Carrageenan Gels", Carbohydrate Polymers, vol. 12, pp. 255-266, 1990.

Informe Technico 26, Macroalgas De Interes Comercial En Las Costas Del Sur De Chubut Y Norte De Santa Cruz, Maria Luz Piriz y Graciela Casas, ISSN N° 0328-462X, 1996. pp. (34). (Partial Translation).

Seasonal variation of carrageenans in tetrasporic, cystocarpic and 'sterile' stages of Gigartina Skottsbergii S.et G. (Rhodophyta, Gigartinales), (Piriz & Cerezo) Hydrobiologia 226: 65-69, 1991, Kluwer Academic Publishers. Printed in Belgium.

Supplemental European Search Report received in EP No. 04759583 dated Jun. 15, 2010.

Declaration of Kevin Stokes Dated Aug. 3, 2010. (unpublished).

* cited by examiner

HOMOGENEOUS, THERMOREVERSIBLE GEL FILM CONTAINING KAPPA-2 CARRAGEENAN AND SOFT CAPSULES MADE THEREFROM

RELATED APPLICATIONS

This application claims the benefit of U.S. Provisional Application No. 60/462,785, filed on Apr. 14, 2003.

FIELD OF THE INVENTION

The present invention is directed to a homogeneous, thermoreversible gel film comprising a film forming amount of kappa-2 carrageenan, and optionally at least one of a plasticizer, a second film former, a bulking agent, and a pH controlling agent; and processes for the preparation thereof. The present invention is also directed to soft capsules and solid forms containing the gel film, as well as processes for the preparation thereof.

BACKGROUND OF THE INVENTION

Gelatin has long been used to form films useful in the preparation of soft capsules. It is a hydrolyzed protein from collagen usually obtained by boiling animal bones and cartilage under pressure with water. However, the use of gelatin suffers from several commercial drawbacks; e.g., its animal origins often preclude its availability to those who cannot or will not take animal derived capsules and recent concerns over bovine spongiform encephalopathy, BSE, or "Mad Cow Disease."

As a result, academia and industry have been trying for many years to develop alternatives to gelatin that can desirably use many of the machines and processes, such as rotary dies, that are already in place to make soft capsules from gelatin alternatives.

For example, Japanese Patent Application Kokai Publication No. 61-10508A discloses capsules made from the composition of polysaccharides including at least carrageenan and polyhydric alcohols. Carrageenan can be used wholly or partly with other polysaccharides such as tamarind gum, pectin, gelatin, alginates, agar, furcellaran, cellulose derivatives, locust bean gum, and guar gum. Polyhydric alcohols include sorbitol, glucose, sucrose, ethylene glycol, diethylene glycol, triethylene glycol, polyethylene glycol, propylene glycol, polypropylene glycol, butane diol and glycerin. The soft capsules are made from concave stamping dies.

Japanese Patent Application Kokai Publication No. 63-164858 discloses mixtures of polysaccharides and polyhydric alcohols with/without alkaline substances. The broad list of polysaccharides purported to be useful in the application include natural polysaccharides such as carrageenan, alginic acid, alginate derivatives, agar, locust bean gum, guar gum, tamarind seed polysaccharides, pectin, xanthan gum, glucomannan, chitin, pullulan and cyclodextrine. The polysaccharides are stated to be combined with a concentrated water solution of at least one of a polyhydric alcohol, sugar alcohol, monosaccharide, disaccharide and oligosaccharide. The mixtures are stated to be useful in forming hulls of soft capsules. The three examples are directed to making hulls of soft capsules having double layers of the mixture with gelatin and a single layer consisting of the mixture of the invention with gelatin. No specific carrageenans are mentioned.

U.S. Pat. No. 5,089,307 discloses heat-sealable edible films comprising at least a film layer containing a water-soluble polysaccharide as the principal component, a polyhydric alcohol and water. The films are stated to be useful for sealing and packaging materials for dried foods, oily foods and the like. The polysaccharides purported to be useful include alginic acid and its salts (such as sodium salt); furcellaran; carrageenan such as kappa-, iota- and lambda-carrageenans; agar; pectin such as high-methoxy and low-methoxy pectins; gums such as tamarind seed gum, xanthan gum, guar gum, tara seed gum, locust bean gum; pullulan; chitin derivatives such as chitosan; starch such as wheat, corn and potato starches; dextrin; edible water-soluble cellulose derivatives such as carboxymethylcellulose; and mixtures of the foregoing. The weight ratio of the polyhydric alcohol to polysaccharide is preferably used in an amount of 1:5 to 1:1, and the polysaccharide is present in an amount of not less than 50% of the total amount of active components. There is no disclosure that such films can be used in the manufacture of soft or hard capsules.

U.S. Pat. No. 6,331,205 discloses aqueous viscous compositions for making soft or hard capsules containing carrageenan, preferably, iota carrageenan as the single gelling agent. Iota-, lambda-, mu-, and nu-carrageenans are disclosed as the types of carrageenans that can be used in the invention, and such are stated to be extracted from a variety of different seaweed sources depending on the extraction method utilized. Plasticizers are disclosed such as those belonging to the polyoxyls class; e.g., glycerol, sorbitol, maltodextrins, dextrose, mannitol, xylitol, polyoxyethylene glycol 400 to 6000, natural glycerides and hemisynthetics and their derivatives, etc. Soft capsules are said to be obtained by an adaptation of the "Scherer" method. Films made from kappa carrageenans are said to have syneresis causing problems in the manufacturing of hard and soft capsules. There is no description of any specific iota carrageenans, kappa carrageenans, kappa-2 carrageenans, etc.

U.S. Pat. No. 6,214,376 discloses gelatin-free capsules made from compositions comprising water-soluble hydrophilic colloidal layers comprising gel films of kappa-carrageenan and a plasticizer. The gelatin free soft capsules are said to be made from kappa-carrageenan as the main gel-forming polymer (at least 50% by weight of gums that form thermoreversible gels or contribute to the formation of thermoreversible gels). Hydrolyzed starches such as maltodextrin may be added to increase solids concentration, aid heat sealing and prevent hazing induced by gelling salts. Other types of gums, such as iota carrageenan, are taught to be minimized, most preferably, to an amount less than 0.5% of the total film composition.

U.S. Pat. No. 6,340,473 requires the use of a modified starch having a hydration temperature below about 90° C. and iota carrageenan for the manufacture of soft capsules using rotary die encapsulation apparatus. The weight ratio of the modified starch to the iota carrageenan is stated to be crucial to forming a satisfactory film. That is, the weight ratio of the modified starch to the iota carrageenan is said to be 1.5:1. The inventors purportedly found that iota-carrageenan alone does not produce an acceptable film and that modified starch alone does not produce an acceptable film useable for encapsulation. The stated theory is that the iota carrageenan functions as an elasticizing agent rendering an otherwise inelastic, modified starch film, elastic. Carrageenans are stated to be complex with hundreds of different products on the market having different functionalities. *Eucheuma spinosum* is stated to be the seaweed source for iota carrageenan, and not all carrageenans are stated to be useable in the invention, e.g., kappa carrageenan is stated not to be a substitute for iota carrageenan therein.

It is known that certain high solids, low moisture film forming compositions containing, for example, hydrocolloids, form highly viscous solutions that make formation of hydrated films difficult to obtain. The present invention provides a process for preparing high solids, low moisture films from such highly viscous solutions.

In addition, many attempts have been made to make soft capsules from high solids, low moisture films such as hydrocolloids. However, such attempts to make soft capsules have suffered from the drawback mentioned above. That is, hydrocolloids are known to form highly viscous solutions that are difficult to sufficiently hydrate and form a film in conventional soft capsule making processes. The process of the invention therefore allows for the manufacture of soft capsules from such films.

SUMMARY OF THE INVENTION

As a first embodiment, the present invention is directed to a homogeneous, thermoreversible gel film comprising a film forming amount of kappa-2 carrageenan, and optionally at least one of a plasticizer, a second film former, a bulking agent, and a pH controlling agent.

As a second embodiment, the present invention is directed to a process for making gel films comprising the steps of: (i) heating, hydrating, mixing, solubilizing and, optionally, de-aerating a composition of a kappa-2 carrageenan and optionally at least one of a plasticizer, second film former, bulking agent and pH controlling agent in an apparatus providing sufficient shear, temperature and residence time to form a homogeneous, thermoreversible, molten composition thereof, wherein the temperature is at or above the solubilizing temperature of the molten composition; and (ii) cooling the molten composition at or below its gelling temperature to form the gel film.

As a third embodiment, the present invention is directed to soft capsules comprising capsule walls and an encapsulated substance wherein the capsule walls comprise the gel films of the present invention, as a well as a process for the preparation thereof. The process comprises the steps of: (i) heating, hydrating, mixing, solubilizing and, optionally, de-aerating, a composition of the kappa-2 carrageenan and optionally at least one of the plasticizer, the secondary film former, the bulking agent and the pH controlling agent in an apparatus providing sufficient shear, temperature and residence time to form a homogeneous, molten composition thereof, wherein the temperature is at or above the solubilizing temperature of the molten composition; and (ii) making soft capsules directly from the molten composition or allowing the molten composition to cool to its gelling temperature or below and thereafter making soft capsules therefrom.

As a fourth embodiment, the present invention is directed to solid forms comprising a fill material encapsulated by the homogeneous, thermoreversible gel film of the present invention; e.g., hard capsules.

DETAILED DESCRIPTION OF THE INVENTION

Figure 1:
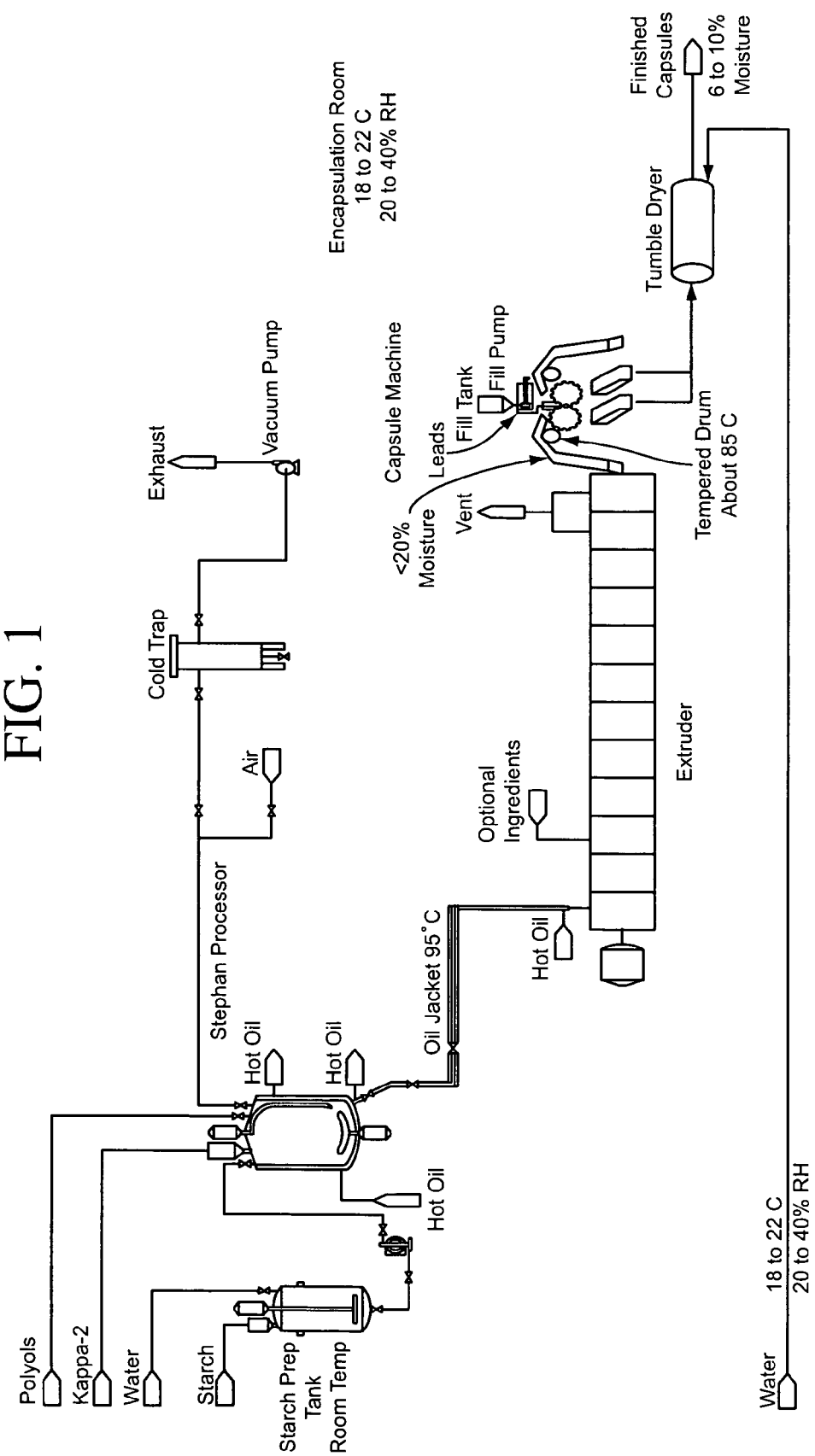
FIG. 1 is a schematic of a process of the present invention to make films and soft capsules using a Stephan processor together with an extruder.
Figure 2:
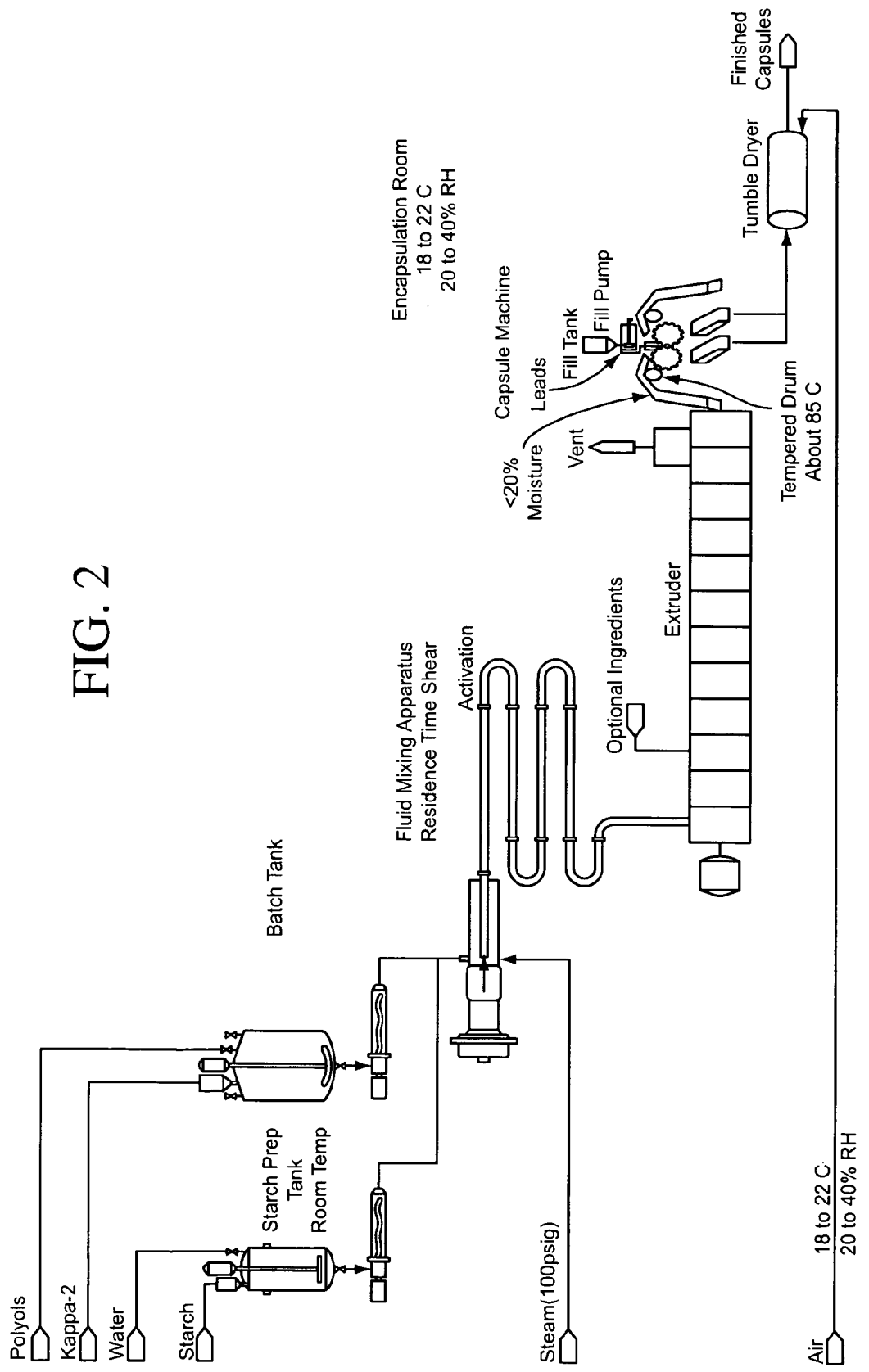
FIG. 2 is a schematic of a process of the present invention to make films and soft capsules using a fluid mixing apparatus of FIG. 3 and an extruder. The schematic shows the film coming out of the extruder proceeding to the encapsulation apparatus.

Carrageenan is a commercially significant galactan polysaccharide found in red seaweed. All carrageenans contain repeating galactose units joined by alternating $\alpha1\rightarrow3$ and $\beta1\rightarrow4$ glycosidic linkages and are sulfated to widely varying degrees. The types of carrageenan may be distinguished, in part, by their degree and position of sulphation, as well as the seaweed from which they are obtained. For example, iota carrageenan has a repeating unit of D-galactose-4-sulfate-3, 6-anhydro-D-galactose-2-sulfate providing a sulfate ester content of about 25 to 34%. Iota carrageenan can be obtained, for example, from *Eucheuma denticulatum* ("also referred to as "*Spinosum*"). Kappa carrageenan has a repeating unit of D-galactose-4-sulfate-3,6-anhydro-D-galactose and is obtained, for example, from *Kappaphycus alvarezii* (also known as "*Eucheuma cottonii*"). In contrast, kappa-2 carrageenan is reported by R. Falshaw, H. J. Bixler and K. Johndro, *Structure and Performance of Commercial Kappa*-2 *Carrageenan Extracts*, Food Hydrocolloids 15 (2001) 441-452, and by H. Bixler, K Johndro and R Falshaw, *Kappa*-2 *carrageenan: structure and performance of commercial extracts II*, Food Hydrocolloids 15 (2001) 619-630 to be copolymers containing a certain amount of kappa repeating units (3:6-anhydroglactose (3:6-AG)) and iota repeating units (3:6-anhydrogalactose-2-sulfate (3:6-AG-2-S)) covalently bound in the copolymer backbone and obtained from certain *Gigartinaceae* algae. The foregoing references state that such kappa-2 carrageenans have distinctly different properties as compared to simple mixtures of kappa and iota carrageenans. Other references discussing kappa-2 carrageenan are discussed in these publications. Kappa-2 carrageenan extracted from *Gigartina atropurpurea* is reported by R. Falshaw, H Bixler and K Johndro, *Structure and Performance of Commercial Kappa*-2 *Carrageenan extracts III*, Food Hydrocolloids 17 (2003) 129-139. While there has been considerable confusion historically about the physical nature of kappa-2 carrageenans, recent studies, such as those mentioned immediately above, have confirmed that kappa-2 carrageenans are copolymers containing kappa and iota repeating units covalently bound (in certain ratios of kappa to iota moieties) in the copolymer backbone in clear distinction to physical mixtures of kappa and iota polymers.

As used herein, kappa-2 carrageenan has a molar ratio of 3:6 AG-2S to 3:6 AG content of 25 to 50%, iota carrageenan has a molar ratio of 3:6 AG-2S to 3:6 AG content of 80 to 100% and kappa carrageenan has a molar ratio of 3:6 AG-2S to 3:6 AG content less than that for kappa-2 carrageenan. For example, kappa carrageenan from *Eucheuma cottonii*, a commonly known and used seaweed source for kappa carrageenan, has a molar ratio of 3:6 AG2S to 3:6 AG content of less than about 10%; and iota carrageenan from *Spinosum*, a commonly known and used seaweed source for iota carrageenan, has a molar ratio of 3:6 AG2S to 3:6 AG content greater than about 85%. This means that kappa-2 carrageenan comprises a ratio of kappa (3:6-AG) repeating units to iota (3:6-AG-2-S) repeating units between 1.0 to 3.0:1, more particularly, 1.5 to 3.0:1 (more particularly depending on the desired application). The molar ratio of 3:6 AG-2S to 3:6 AG content of 25 to 50% holds in kappa-2 carrageenans regardless of its degree of modification and precursor content (e.g, mu and nu repeating units). Thus, any kappa-2 carrageenan meeting the molar ratio of 3:6 AG-2S to 3:6 AG content of 25 to 50%, regardless of its degree of modification, is within the scope of this invention.

The kappa-2 carrageenan to be used in the present invention may be contained within or purified or separated from a number of seaweed species within the class of, for example, *Gigartinaceae* algae such as *Gigartina radula*, *Gigartina corymbifera*, *Gigartina skottsbergii*, *Iridaea cordata*, *Sarcothalia crispata*, and *Mazzaella laminarioides*. The seaweed source of the kappa-2 carrageenan to be used in this invention is any that produces kappa-2 carrageenan having the molar content of 3:6 AG-2S to 3:6 AG described herein. The kappa-2 carrageenan that can be used in the present invention may occur naturally in the seaweeds above or may be modified from the above seaweeds to increase the amount of 3:6 AG-2S and 3:6 AG moieties in the kappa-2 carrageenan from their precursors (e.g., 3:6 AG-2S moiety within the kappa-2 carrageenan modified from its precursor nu upon alkali treatment, and 3:6 AG moiety within the kappa-2 carrageenan modified from its precursor mu upon alkali treatment). The recovery and modification techniques are well known in the art including the cited publications by Falshaw, Bixler and Johndro. For example, modification of the kappa-2 carrageenan can occur during its recovery from certain *Gigartinacean* algae as a result of alkali treatment at elevated temperatures. Recovery methods include the optional full or partial filtration of insolubles from the starting material or the use of unfiltered material. When the nu and mu precursors in the kappa-2 carrageenan are modified to 3:6 AG-2S and 3:6 AG, respectively, such modification may be complete (i.e., 100% of the nu and mu precursors in the kappa-2 carrageenan are modified to 3:6 AG-2S and 3:6 AG moieties, respectively) or less than fully complete (i.e., less than 100% of the nu and mu precursors in the kappa-2 carrageenan are modified to 3:6 AG-2S and 3:6 AG moieties, respectively). It is understood that during the recovery process of the kappa-2 carrageenan from the above seaweeds small or trace amounts of other carrageenans may be present (e.g., lambda carrageenans) and such can be used with the kappa-2 carrageenans in the present invention.

One of the surprising aspects of the present invention is the functionality of the kappa-2 carrageenan as compared to kappa carrageenans, iota carrageenans and simple dry mixtures of kappa and iota carrageenans that contain the identical level of 3:6-AG-2-S. That is, iota and kappa carrageenans are gelling carrageenans. In distinction, kappa-2 carrageenans are known to be weakly gelling. As a result, it would have been expected that such weakly gelling carrageenans would form weak gel films. However, to the surprise of the Applicants, kappa-2 carrageenans have been found to form surprisingly strong gel films.

Without being bound, it is generally recognized that the water gel strength of kappa carrageenan decreases significantly as 3:6-AG-2-S content increases (e.g. 1,500 g to 300 g at 1% in water), this being due to the structural interference of these additional ester sulphates with helical aggregation and hydrogen bonding between such aggregated helices. This trend continues for kappa-2 (25-50%, more particularly 25-40% 3:6-AG-2-S for particular applications), with water gels as low as 150 g and is likely due to its structural variability. Iota carrageenan (e.g., 80 to 100% 3:6-AG-2-S), however, is more ordered structurally, thereby contributing a more uniform three dimensional structure to this water gel, providing a stronger water gel, as indicated by its rupture strength of over 300 g. While not bound by any theory, it is thought that simple physical mixtures of kappa and iota carrageenans are somewhat antagonistic with respect to gel strength, most likely due to mutual interference of their ideal gel structures developed at separate temperatures upon cooling. Resultant gel strength values for the dry blended, physical mixtures of kappa and iota carrageenan based water gels are still much higher in water gel strength than kappa-2 carrageenan. One can also achieve this antagonistic effect by separately hydrating & solubilizing the kappa and iota carrageenans, and, while maintaining their solutions above their gelling temperatures, uniformly combine solutions and cast or allow the blend to cool to initiate gelation. This gel strength drop (structural weakening) is further aggravated by extract viscosity reduction (shorter molecules) and divalency addition. Thus, based on traditional gel strength and textural measurement, kappa-2 carrageenan would not be expected to be appropriate for gel film applications.

However, as the inventors here found, when kappa-2 is applied to making gel films, it demonstrates surprising film strength and mechanical integrity, well beyond expectations based on traditional (prior art) molecular structuring with respect to water gels. It also demonstrates full compatibility with traditional film and capsule film ingredients, such as starch, humectant, etc. It is thought that the random copolymeric gel structure of kappa-2 carrageenan in such gel films and film compositions is ideal, contributing complete structural stability from the onset of gelation, with no need or tendency to change over time or during film drying process. The structure stays as it is gelled, unlike kappa carrageenan structure that continues to harden, iota carrageenan that is too elastic and won't tighten, and kappa/iota physical blends (as opposed to kappa-2 copolymers) that exhibit structural interferences. This surprising film strength of kappa-2 carrageenan also allows carrageenan molecular weight control in order to better balance process viscosity and required film strength for mechanical processing into capsules, such direction resulting in the capability to operate at lower moisture levels in the cast films while maintaining other essential film properties.

The kappa-2 carrageenan is used in the present invention in a film forming amount (e.g., an amount that adds film strength to the gel film) which is distinguished from trace amounts of kappa-2 carrageenan that do not add film properties to the film. Thus, for example, in a gel film of the present invention containing the second film formers discussed below, a film forming amount of kappa-2 carrageenan is an amount that adds film strength to the overall film. Such film forming amounts are generally at least 0.5% by weight of the dry gel film, particularly, 0.5% to 90%, more particularly, 0.5% to 50%, more particularly, 0.5% to 25%, more particularly, 1.5 to 25% by weight of the dry gel film depending on the application.

As used herein, "homogeneous film" defines films that, to the naked eye, are visually uniform and free of defects such as lumps, cracks, particles that are undissolved that should be dissolved, non-uniform distribution of insoluble particles, etc. "Fish eyes" (mixed liquid and solid states) or "gel balls" (non-uniform gel structure) would not meet the definition of "homogeneous" as used herein.

The gel films of the present invention are homogeneous, thermoreversible gel films. They can be cast and used in a wide variety of applications as cast films or in subsequent processing.

As used herein, "thermoreversible film" defines a film that has a melting temperature. As used herein, the melting temperature is the temperature or temperature range over which the gel film softens or flows.

As used herein, the phrase "gel films" refer to a thin membrane or three dimensional network, formed from structured kappa-2 carrageenan. The gel-forming composition is characterized by a gel temperature, the temperature below which the molten mass of the gel composition must be cooled to form a self-supporting structure. Optionally, a molten mass can be cast hot and allowed to cool, as well as dry to further concentrate the solids (controlled moisture removal) until a gel film is formed by the gel composition. The melt temperature of a thermoreversible gel film is higher than its gel temperature.

The gel film of the present invention desirably contains soluble gelling cations that promote carrageenan structure formation; i.e., gel formation. Such beneficial cations include potassium, sodium and ammonium. These cations can be present within the kappa-2 carrageenan or added to it from other organic or inorganic sources, at various points in the process, while maintaining the molten mass above its gelation temperature. These beneficial cations can be present in an amount of less than 50% by dry weight of the kappa-2 carrageenan in the gel film (including water). This amount can be varied depending on the components in the system, desired melt and sealing temperatures, and processing conditions and equipment choices.

Other soluble cations, such as calcium, magnesium, aluminum and chromium can adversely impact stability and should be kept to a minimum, such as less than 10%, less than 5%, less than 1% by dry weight of the kappa-2 carrageenan in the gel film (including water). Sequestering or chelating agents could be added in sufficient amounts to minimize the above cation solubility (and participating activity), providing the gel system is not adversely affected by the sequestering agent nor the resulting compound.

The molecular weight of the kappa-2 carrageenan is generally above 100,000 Daltons, preferably, 100,000 to 1,000,000, more preferably, 100,000 to 450,000, more preferably, 100,000 to 350,000 depending on the application.

In some applications, reducing the gelling temperature of the kappa-2 carrageenan is desirable. A gelled system of kappa-2 carrageenan having an average to high molecular weight has a gelling temperature of at least 59° C. and 35° C. in the potassium/calcium and sodium forms, respectively. Thus, replacing the potassium cation with sodium cation is one way to reduce the gelling temperature of kappa-2 carrageenans. It has generally been considered that the gelling temperature is independent of the molecular weight of the kappa-2 carrageenans. However, surprisingly, Applicants have further discovered that in high solids systems having at least 50% solids, using a kappa-2 carrageenan having a reduced molecular weight (e.g., having a viscosity of 19 cps or less, more particularly less than 10 cps, at 75° C. in a 0.10 molar sodium chloride solution containing 1.5% of the reduced molecular weight carrageenan by weight based on the total weight of the solution; this viscosity test can be performed using a Brookfield LVF (Brookfield Engineering Laboratories, Inc.) viscometer using Spindle #1 at 60 r.p.m. and determining the viscosity after six revolutions) can further reduce the gelling temperature of kappa-2 carrageenan, for example, from 35° C. to 25° C. in the sodium form and from 59° C. to 57° C. in the potassium/calcium form. Reducing the gelling temperature of the kappa-2 carrageenan generated structure can have beneficial effects in the processing of the gel films of the present invention, for example, in making soft capsules, hard capsules and other solid forms, by lowering the amount of heat used in the manufacturing process and minimizing residual stress on the dried film.

The homogeneous, thermoreversible gel film of the present invention can optionally contain at least one of a plasticizer, a second film former, a bulking agent and a pH controlling agent. The components to be added to the gel film and their amounts can vary depending on the desired use of the kappa-2 gel film.

Examples of such a plasticizer include polyols such as glycerin, sorbitol, maltitol, lactitol, corn starch, fructose, polydextrose, solubilized oil and polyalkylene glycols such as propylene glycol and polyethylene glycol. The amount of the plasticizer can vary depending on the use of the gel film and its desired elasticity. For example, such plasticizers can generally be used in an amount of at least 5%, more preferably, at least 10%, more preferably, at least 20%, more preferably, at least 30% by weight of all the components including water in the dry film if a gel film having more elasticity is desired; e.g., films to be used to make soft capsules. For other applications, such as hard capsules, where less elastic films are desired, the plasticizer can be present in an amount of 0% to 20% by weight of all the components in the dry film. It is possible that the gel film of the invention contains no plasticizer at all.

Examples of the second film former that can be used in the present invention include at least one of a starch, starch hydrozylate, starch derivative, cellulose gum, hydrocolloid, an alkylcellulose ether or a modified alkyl cellulose ether. Examples of the hydrocolloid include at least one of kappa carrageenan; iota carrageenan; kappa and iota carrageenans having a reduced molecular weight (e.g., having a viscosity of 19 cps or less, more particularly less than 10 cps, at 75° C. when measured in a 0.10 molar sodium chloride solution containing 1.5% of the reduced molecular weight carrageenan based on the total weight of the solution; this viscosity test can be performed using a Brookfield LVF (Brookfield Engineering Laboratories, Inc.) viscometer using Spindle #1 at 60 r.p.m. and determining the viscosity after six revolutions) and less than fully modified versions thereof; alginates including potassium alginate, sodium alginate, ammonium alginate and propylene glycol alginate; polymannan gums (e.g., generally less than about 1000 mPs viscosity as measured at 1 wt % in water at 25° C.) such as low viscosity guar gum; pullulan, gellan (including high and low-acyl gellan); dextran; pectin and combinations thereof. An example of an alkylcellulose ether that can be used in the present invention is hydroxyethylcellulose. Examples of modified alkylcellulose ethers that can be used in the present invention include hydroxypropylcellulose and hydroxypropylmethylcellulose. The kappa-2 carrageenan can be the only film former in the gel film. When the gel films of the present invention contain second film formers, the kappa-2 carrageenan can be present in an amount of at least 10%, at least 20%, at least 50% or at least 80% by weight of the total amount of film formers in the dry gel film.

A dried film is the residual form of a cast film after controlled water removal. Combinations of ingredients, such as: kappa-2 carrageenan, and, optionally, a starch, a polyol and water for processing, are dispersed, hydrated, solubilized and, optionally, de-aerated within the process options described within. The resulting homogeneous mass is cast or formed at the desired solids level (necessary to achieve the intended end-product). The cast system is formed, via gravitational or controlled forces, and subsequently either immediately further processed (such as soft gel capsule production) or the cast mass is additionally processed by utilizing various methods for uniform and controlled water removal until the desired moisture level is reached. Controlled water removal from the cast system allows a further strengthening/alignment of the homogeneous film ingredients into a denser structure, which can further strengthen film characteristics. Moisture removal is limited to that moisture not bound to the molecular surface of the various hydrocolloid and carbohydrate components. The dried film is achieved when the originally cast film does not lose additional weight while subject to the various drying methods employed in the dewatering/dehydration process. A reduction in moisture content to constant levels also imparts stability to the film and, optionally, its contents (if embedded or enrobed or entrapped, etc.) as water activity is also reduced by the process.

Examples of the bulking agent include non-colloidal (vegetal sourced) cellulose, microcrystalline (vegetal sourced) cellulose, microcrystalline starch, modified and unmodified starch, starch derivatives and fractions, inulin, starch hydrozylates, sugar, corn syrup and polydextrose. As used herein and in the claims, the term "modified starch" includes such starches as hydroxypropylated starches, acid-thinned starches, and the like. Examples of modified starches that can be used in the present invention include Pure Cote™ B760, B790, B793, B795, M250 and M180, Pure-Dent™ B890 and Pure-Set™ B965, all available from Grain Processing Corporation of Muscatine, Iowa, and C AraTex™ 75701, available from Cerestar, Inc. Examples of starch hydrozylates include maltodextrin also known as dextrin. Unmodified starches such as potato starch can also contribute to the film strength when combined with the hydrocolloids within the scope of the invention. In general, modified starches are products prepared by the chemical treatment of starches, for example, acid treatment starches, enzyme treatment starches, oxidized starches, cross-bonding starches, and other starch derivatives. It is preferred that the modified starches be derivatized wherein side chains are modified with hydrophilic or hydrophobic groups to thereby form a more complicated structure with a strong interaction between side chains.

The amount of the bulking agent to be used in the present invention is generally in the amount of 0 to 20% by weight of the dry film, but more can be used, if desired, for example, at least 20%, more preferably, at least 30% by weight of the dry film.

Note that starch, starch derivatives and starch hydrozylates can be multifunctional. That is, in addition to being used as bulking agents, they can be used as second film formers. When such are used as bulking agents and second film formers, they are generally used in an amount of at least 10%, preferably, at least 20%, more preferably, at least 30% by weight of the dry gel film depending on the application; e.g., soft capsules.

Examples of the pH controlling agent that can optionally be used in the present invention include bases such as hydroxides, carbonates, citrates and phosphates, mixtures thereof and their salts (e.g., sodium citrate). The pH controlling agent can be chosen as the source of added beneficial cations such as potassium or sodium. For some compositions, the pH controlling agent can be used to improve the stability of the gel film. The amount of the pH controlling agent is generally in the amount of 0 to 4%, preferably, 0 to 2%.

The gel films of the invention can also contain colorants and flavorants such as sugar, corn syrup, fructose, sucrose, aspartame, sucralose, sorbitol, mannitol, maltitol, etc, whether or not other components, such as plasticizers, bulking agents, second film formers, etc. are present. One embodiment of a gel film of the invention comprises kappa-2 carrageenan, flavorant and water in a high solids system; e.g., greater than 50%, 60%, 65%, 75%, 80%, 85%, 90% solids.

The dry gel films (e.g., 80% solids or higher) of the present invention have been found to have, for example, a break force of at least 1,500, at least 2,500 grams, at least 4,000 grams, at least 5,000 grams and at least 6,000 grams, as determined using a Texture Analyzer TA-108S Mini Film Test Rig. At lower solids, the gel films have been found to have a break force of at least 50 grams, at least 100 grams, at least 200 grams, at least 500 grams, at least 1000 grams, as determined in a similar manner.

The films of the present invention have been found to have a solids content of at least 50%, at least 60%, at least 70%, at least 80% and at least 90% of all components in the gel film. It is understood that 15%, 10% or 5% water may remain strongly associated with the solids in the dry gel film.

Dry film thicknesses generally used for soft capsules are in the range of 0.5 to 3.0 mm, more preferably, 0.8 to 1.2 mm.

It is possible that the gel films of the present invention can contain nonthermoreversible gums. However, so as not to adversely impact the homogeneous and thermoreversible nature of the gel films of the present invention, such nonthermoreversible gums should be present in an amount of less than 50% by weight of the kappa-2 carrageenan, preferably, less than 40%, more preferably, less than 30%. Examples of such nonthermoreversible gums include crosslinked gums such as calcium set (e.g., crosslinked) pectins and/or alginates. Calcium reactive alginates and pectins, as well as their less refined forms, are considered as thermoreversible gums in the absence of divalent cations. Other non-thermoreversible gums such as tragacanth gum contribute to the thermoreversibility of the kappa-2 carrageenan by absorption of water within its structure thereby causing the kappa-2 carrageenan to form a denser, three-dimensional structure, as it is solubilized in less water, providing the same effect as increasing the kappa-2 carrageenan amount without the secondary film formers. Additional film formers, such as polymannans can form continuous networks, either by themselves or synergistically with other components during the activation and casting process.

The kappa-2 carrageenan gel films of the present invention are generally made from a process utilizing an apparatus that enables sufficiently high shear, temperature (above the gelling temperature) and residence time so as to provide a homogeneous molten mass of the composition and formation of the gel upon cooling. Such apparatus include but are not limited to Ross mixers, Stephan processors, conventional jet cookers, extruders and the fluid mixing apparatus as set forth in FIG. 3. Ross mixers, Stephan processors, extruders and conventional jet cookers are readily available commercially. Prior to cooling, the molten mass can be fed to at least one of a pump, mixer or devolatilizer. An example of a device that performs any one of such functions is an extruder. An extruded molten mass can also be directed to a film forming or shaping device (e.g. spreader box, as used in a capsule forming machine) that aids in the uniform casting of a continuous film, or, through a die that allows a direct formation of a film or shaped extrudate from the molten mass delivery equipment. Care must be taken to maintain the molten mass above the initiation of restricted flow/gel structure formation. Insulated and pre-heated (to maintain proper temperatures) transfer hoses may be used to insure molten mass flow until desired gel film formation is initiated on the casting rolls or at other film formation points, such as an extruder (restrictive flow, film forming device) or die. Additional processing methods (such as pre-heating the discharge/plunger-like head as seen in a Ross process system) can force (by pressure) the molten mass through the transfer hoses mentioned above. Additional insulation can help maintain molten mass temperatures through the use of a Teflon disk initially placed upon the molten mass surface immediately after removing the mixing device. In addition, the feeder hoses can be introduced to the heat controlled molten mass feeder (casting) boxes located on a capsule machine either directly to the boxes or through an optional modification of the feeder boxes which introduces a top half enclosure/cover that helps maintain molten mass temperatures within the feeder box, reduces moisture loss, and maintains uniform (center) filling of the box during the extended process of forming films for capsules. It is understood that other methods of maintaining molten mass temperatures can be used to form films for capsules. This includes, but is not limited to: Extrusion of the molten mass through dies/orifices into films that: can be immediately fed into the capsule forming apparatus, stored at temperatures that maintain proper film conditions (to form capsules) until needed, or dried to desired moisture, solids and texture levels, until needed. Such dried films have the property of re-absorbing water (water is introduced by any means) throughout its gel film matrix and can be rehydrated when needed, for example, to make soft capsules or other solid forms. Moisture is introduced to the film until a desired moisture content and strength/texture is reached that will allow the film's introduction into a capsule machine to make soft capsules.

Figure 3:
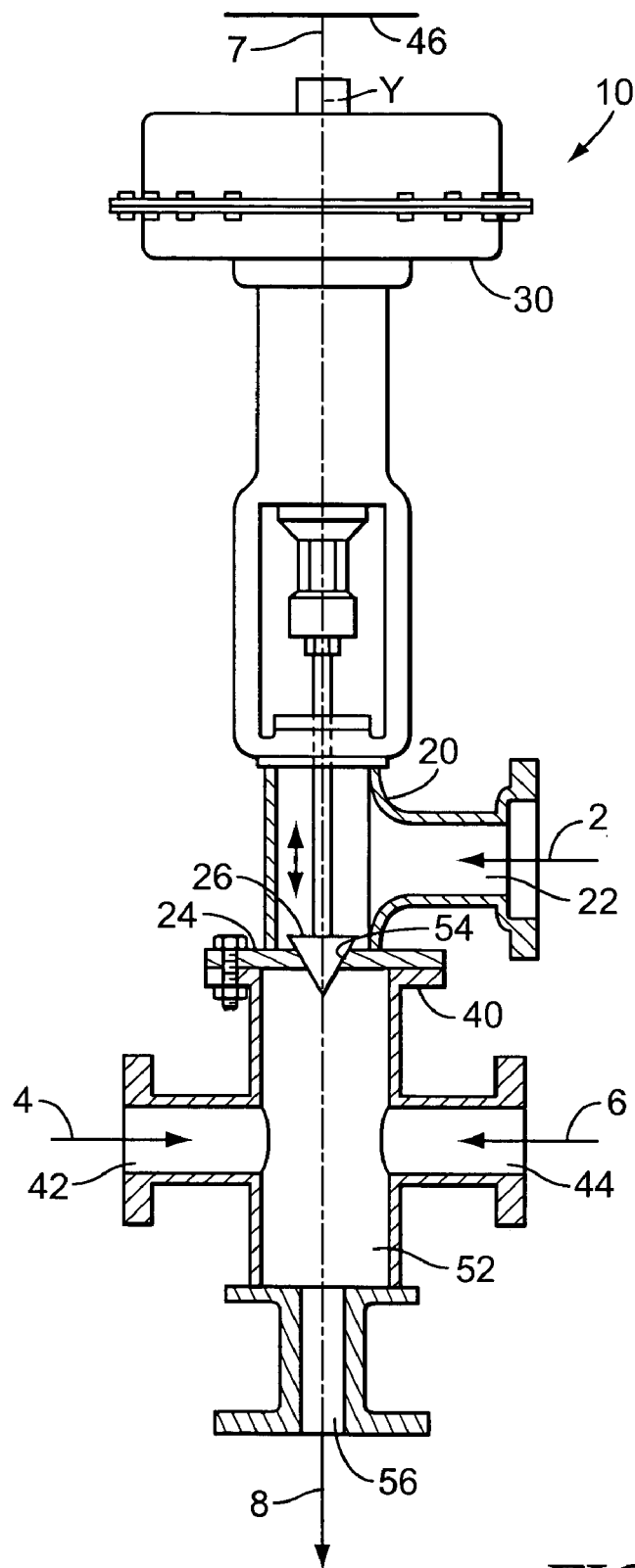
FIG. 3 is a partially broken away, side elevational view of the fluid mixing apparatus for mixing first and second fluids with steam that can be used in the process of the present invention.

As used herein, a "fluid mixing apparatus" refers to the apparatus in FIG. 3. FIG. 3 illustrates a fluid mixing apparatus 10. The fluid mixing apparatus 10 is arranged to mix steam 2 with a first fluid or slurry 4 and a second fluid or slurry 6 to produce a molten mass or slurry mixture 8.

The fluid mixing apparatus 10 comprises a first housing 20 having a first inlet 22 through which the steam 2 enters the housing 22, a nozzle end 24 from which the steam 2 exits the housing 20, and a nozzle valve or stem 26 disposed at the nozzle end 24. An actuator means 30 is connected to the first housing 20 for controlling the exit rate or exit pressure of the first fluid 2 at the nozzle end 24. The actuator means 30 may be of the type manufactured by Fisher Controls U.S.A.

The fluid mixing apparatus 10 further comprises a second, mixing housing 40 coupled to the first housing 20 at the nozzle end 24 of the first housing 20. The second housing 40 includes a second inlet 42 through which the first fluid 4 enters the second housing 40, and a third inlet 44 through which the second fluid 6 enters the second housing 40. The inlets 42 and 44 are disposed downstream of the first inlet 22. As shown in FIG. 3, the second inlet 42 and third inlet 44 are disposed in a common plane and spaced apart radially from each other, most preferably directly opposite (i.e., 180° apart) about the central axis Y of the mixing apparatus 10. The second housing 40 defines a generally cylindrical mixing chamber 52 that in turn defines a flow passage extending along the axial length of the mixing chamber 52 from an entry end 54 of the mixing chamber 52 to an exit end 56 of the chamber 52. The nozzle valve 26 is movable by the actuator 30 between seated and unseated positions at the entry end 54 to control the flow rate of steam 2 into the mixing chamber 52.

The nozzle end 24 of the first housing 20 directs the steam 2 into the entry end 54 of the mixing chamber 52. The second inlet 42 and the third inlet 44 radially direct the first fluid 4 and second fluid 6, respectively, into the mixing chamber 52. The steam 2, first fluid 4 and second fluid 6 are mixed in the mixing chamber 52 to form a molten mass or mixture 8 which exits the mixing chamber 52. The molten mass 8 then may be shaped into a shaped article or formed into a film, such as by casting the mixture 8 onto a cooling drum or by passing the mixture 8 through an extruder.

Figure 4:
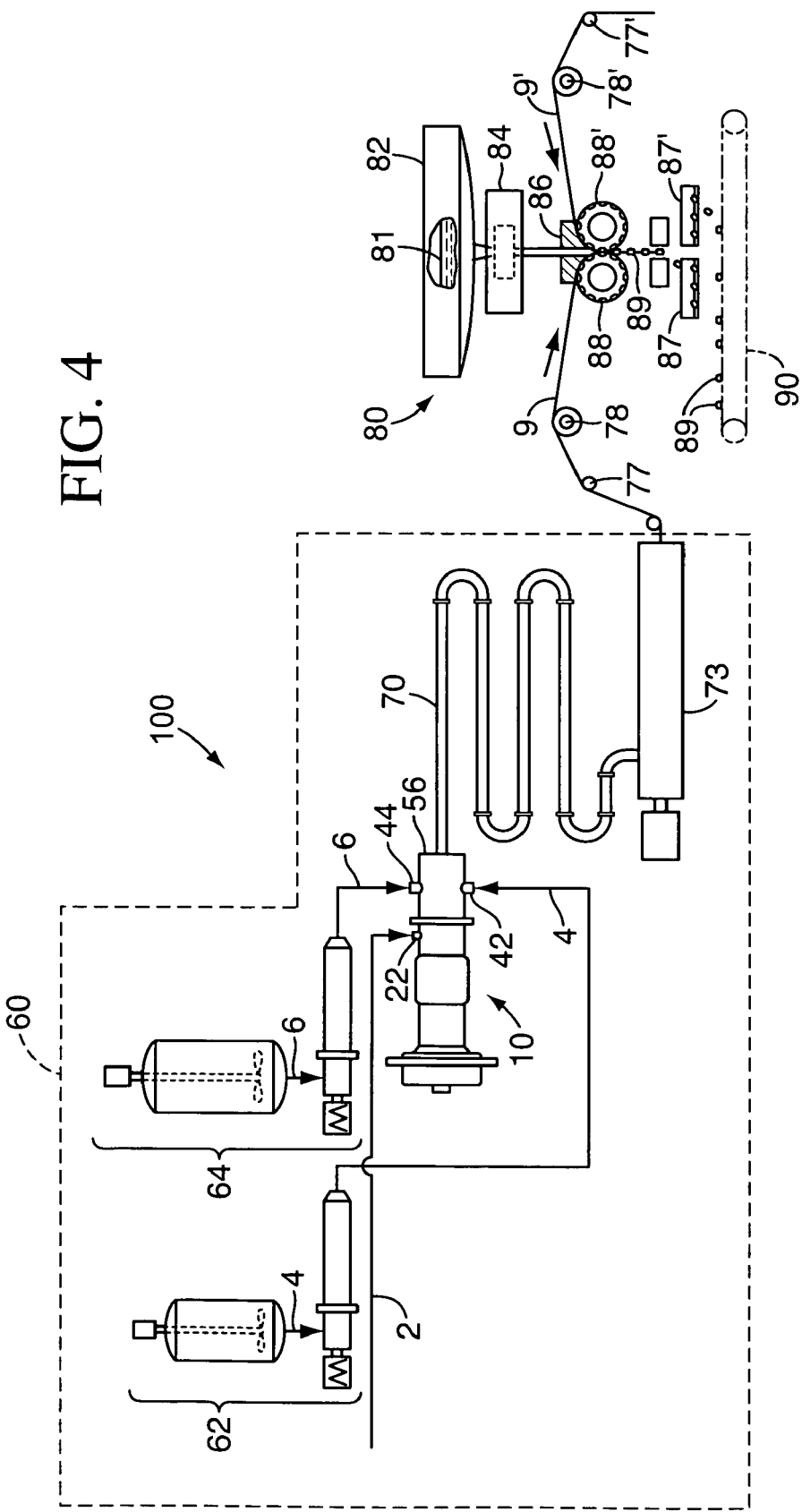
FIG. 4 is another version of the schematic of FIG. 2 showing the film coming out of the extruder proceeding to the encapsulation apparatus.

Referring next to FIG. 4, a system 100 for making films and capsules with the fluid mixing apparatus 10 includes a film preparation unit 60 for preparing and supplying a film 9, and a capsule machine 80 for forming capsules 89. The film preparation unit 60 includes: the fluid mixing apparatus 10; a first fluid supply means 62 for supplying the first fluid 4 to the fluid mixing apparatus 10; a second fluid supply means 64 for supplying the second fluid 6 to the fluid mixing apparatus 10; a slurry mixture supply path 70 for supplying the molten mass or slurry mixture 8 from the fluid mixing apparatus 8 to a shaping apparatus; an optional extruder 73 in fluid communication with the mixture supply path 70 that extrudes the mixture 8 into a film 9; a capsule machine 80 for forming capsules 89; and a conveyor belt 90 for transporting the filled capsules 90 to a subsequent process, such as drying or packaging. The extruder 73 may be of the type manufactured by Wenger or Clextrel.

The capsule machine 80 may be a conventional rotary die capsule machine of the type manufactured by R.P. Scherer Technologies of Paradise Valley, Nev. As shown in FIG. 4, the capsule machine 80 includes a capsule product storage tank 82 that holds a capsule product 81 to be encapsulated. The capsule product 81 may include liquid, semi-liquid or powder pharmaceuticals, vitamins, nutritional supplements, paint balls, pigments, agricultural actives and pre-measured food additives. The capsule machine 80 may be coupled to one or more rollers 77, 77' and 78, 78' so that the films 9, 9' may be drawn into the capsule machine 80. The film 9 is fed between heater block 86 and roller die 88. Portions of the film 9 are drawn by vacuum into recesses formed in the surfaces of the rotary die 88. An amount of the capsule product 81 is delivered into the compartment formed in the film 9 by the vacuum action. Further rotary motion of the dies 88, 88' seals the films 9, 9' together in the nip between the rotary dies 88, 88'. Filled capsules 89 drop into bins 87, 87' and are presented to conveyor 90 for drying and packaging.

Figure 5:
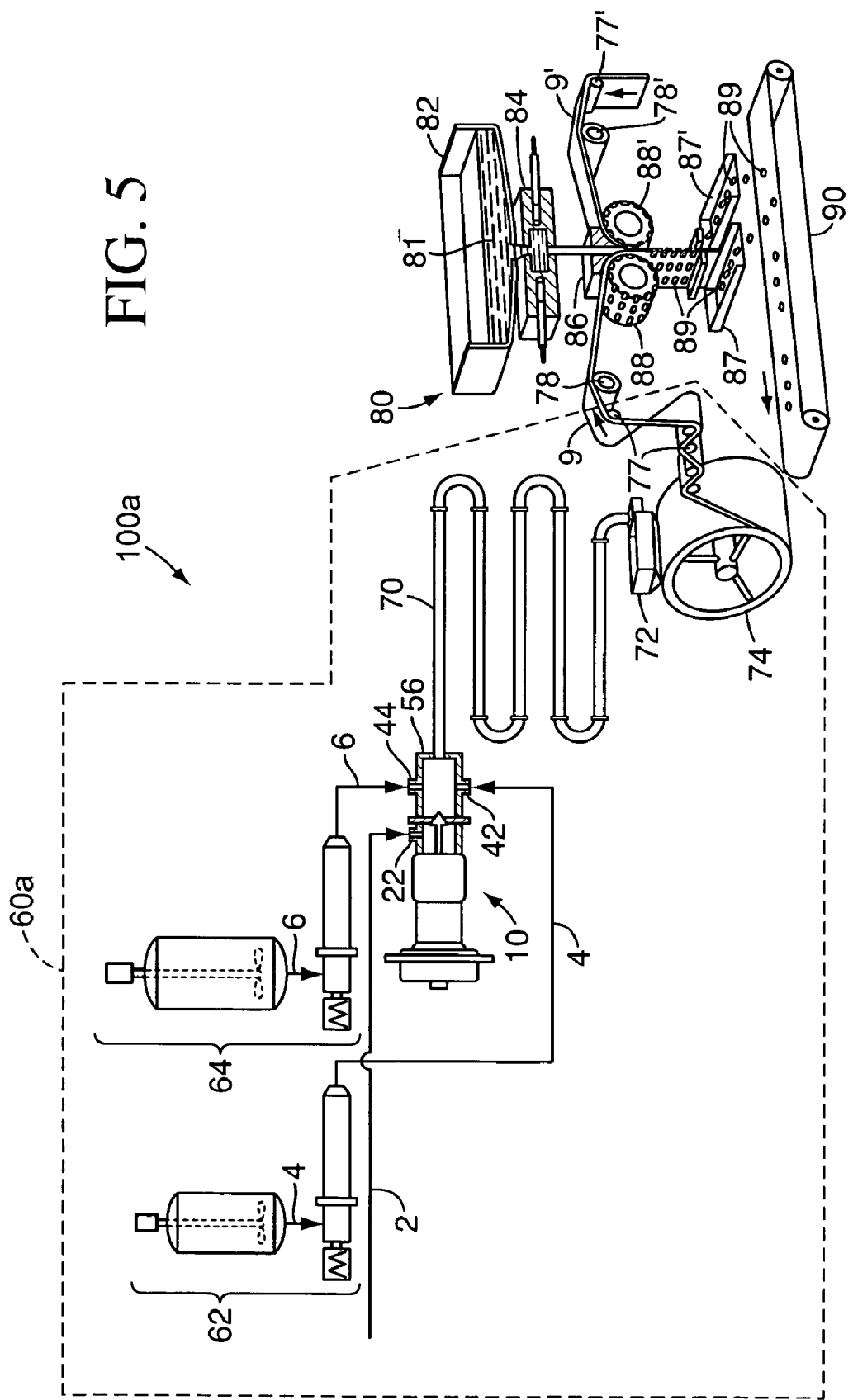
FIG. 5 is a schematic of a process of the present invention to make films and soft capsules using the fluid mixing apparatus of FIG. 3, a cooling drum and an encapsulation apparatus.

Referring next to FIG. 5, a capsule making system 100a is similar to that shown in FIG. 4, wherein like reference characters refer to like elements. In FIG. 5, however, the film preparation unit 60a includes an optional spreader box 72 and an optional cooling drum, or casting drum 74 in place of the extruder 73 of the system in FIG. 4. The system 100a includes a fluid mixing apparatus 10 and a mixture supply path 70 to direct the slurry mixture 8 away from the fluid mixing apparatus and to the spreader box 72. The spreader box 72 spreads the mixture 8 onto the casting drum 74. The film 9 is formed on the casting drum 74 as the mixture 8 cools. Thereafter, the film 9 is fed to the capsule machine 80. The film 9' preferably is formed in the same manner as the film 9 by a second film preparation unit (not shown).

The fluid mixing apparatus 10 is adapted to produce a mixture for forming a film, more particularly an edible film for making edible capsules or strips. Incompatible film components generally are placed in different fluid inlet streams so that such incompatible components come together in the first instance at the interface of the steam injection within the mixing chamber 52 of the fluid mixing apparatus. While FIG. 3 shows inlets for steam, and first and second fluids, one or more additional inlets for one or more additional fluids may be provided. Preferably, the housings 20, 40 and other components of the fluid mixing apparatus 10 are constructed of high-grade stainless steel.

As another aspect of the invention, it is noted that the molten mass need not necessarily reach homogeneity in step (i). That is, homogeneity of the molten mass can be obtained prior to or after feeding the molten composition into at least one of the mixer, pump or devolatilizer provided the molten mass reaches homogeneity prior to gelling.

Since the gel films of the present invention have been shown to have dry film strengths of at least 2,500 grams, they are well suited to make soft capsules. Thus, the present invention is also directed to soft capsules made from the homogeneous, thermoreversible kappa-2 carrageenan gel films of the present invention, as well as methods of making such soft capsules.

The process for making soft capsules from the kappa-2 carrageenan gel films of the invention includes the use of any conventional encapsulating apparatus, e.g., a conventional rotary die apparatus or concave stamping die. For example, once the molten mass of the present invention has been made, it can be cast onto drums, cooled and then fed between rotary encapsulation dies where the films are heated again, filled, sealed and cut. For a good description of this conventional process, see WO 98/42294. Alternatively, and as benefit of the present invention over conventional soft capsule processes, the use of the high shear apparatus disclosed above allows the molten mass to be sufficiently hydrated, applied to drums as they are cooling and then fed into conventional encapsulating apparatus for filling, sealing, and cutting. This continuous type process can be used to eliminate the step of having to reheat fully gelled and cooled films. The above rotary die process can be used to make soft capsules of the invention having any desired shape.

The fill materials for the soft capsules can be any materials widely used in the above rotary die process, including pharmaceutical ingredients, agricultural ingredients, nutraceutical ingredients, veterinary ingredients, foods, cosmetics, personal care, industrial, etc. and can be a liquid, solid, suspension, dispersion, etc.

The present invention is also directed to a solid form comprising a fill material encapsulated by the homogeneous, thermoreversible gel film of the present invention. One type of such solid form is a hard capsule. Hard capsules, as used herein, refer to those solid forms that are conventionally used, e.g., in the pharmaceutical industry whereby two half shells are formed, a fill material, usually a powder, is placed in the shells and the two halves are placed together to form the hard capsule. One process for making such hard capsules would typically involve dipping metal pins or bars into the molten composition of the present invention and allowing the gel film to form around the pins. The gel films are dried and then removed from the pins. These processes are well known in the industry as methods of making hard capsules. The fill materials for the hard capsules can be any fill materials commonly used in such dosage forms. Generally, the fill materials can be liquids (including emulsions) or solids such as powders. The fill materials can be a pharmaceutical ingredient, agricultural ingredient, nutraceutical ingredient, veterinary ingredient, food, cosmetic ingredient, etc.

The solid form may also encapsulate a powder, tablet, caplet, microcapsule or capsule in accordance with known techniques. For example, encapsulating a hard capsule with the gel film of the invention would allow for safety seal/tamper resistant capabilities.

The gel film can also be used to modify the dissolution profile of the dosage forms. For example, gel films of the invention can contain added components that can create solid dosage forms having immediate release, controlled, enteric or delayed release capabilities or can be released upon activation by a known event, condition or process. Definitions of "immediate release", "delayed release" and "enteric" can be found in the U.S. Pharmacopeia and are incorporated herein by reference.

The present invention is now described in more detail by reference to the following examples, but it should be understood that the invention is not construed as being limited thereto. Unless otherwise indicated herein, all parts, percents, ratios and the like are by weight.

EXAMPLES

Unless otherwise indicated, the following procedures were used to prepare and evaluate the materials and films in Examples 1-4. The Stephan UMC5 processor is a laboratory scale mixing device which provided suitable high shear mixing, heating, and de-aerating of the formulations which were cast as films in the laboratory. A suitable batch size used with the Stephan UMC5 processor was 1500 grams.

An aqueous starch dispersion was prepared by dissolving any salts/buffers and pH modifiers in deionized water. The starch and/or maltodextrin (M100) were added and mixed until dissolved/dispersed. Pure Cote® B760 and B790 starches are available from the Grain Processing Corporation of Muscatine, Iowa.

A hydrocolloid mixture was prepared in the Stephan UMC5 processor by premixing the plasticizers until uniform, and adding the preblended dry hydrocolloids portionwise while mixing for about 30 second at 200 rpm after each addition. Sorbitol Special and glycerin were used as plasticizers. Sorbitol Special is an aqueous solution of sorbitol and sorbitol anhydrides at 76% solids supplied by SPI Polyols, Inc (New Castle, Del.).

The starch dispersion was added to the non-aqueous hydrocolloid mixture and mixed at 300 rpm for 5 minutes. The mechanical agitation was increased to 2100 rpm and the mixture was heated to 85° C. to 95° C. with mixing. When the target temperature was achieved, the mixture was stirred for 30 minutes, then the sample was held under vacuum (50-60 bars) with continued agitation for an additional 45 minutes.

When the hold time under vacuum at temperature has been completed, the sample was poured into a preheated wide mouth quart Mason jar. Temperature and pH were recorded. Viscosity was measured on the hot sample using a Brookfield LVF viscometer.

A small portion of the sample was set aside and refrigerated usually overnight prior to measurement of gel/melt properties and solids using an Atago E series hand held refractometer (Gardco, Pompano Beach, Fla.). The melt temperature was determined by placing a small chunk of the refrigerated gel on a wire string stand held within a test tube so that the chunk does not contact the wall of the test tube. The test tube was covered with aluminum foil with a small hole to allow measurement of the gel temperature using a digital Tempermeter probe. The test tube was immersed in the heating bath so that the chunk is below the surface of a hot water bath at approximately 100° C. A silicone oil bath was used for samples that had melt temperatures above 90° C. The melt temperature was recorded when the gelled sample became wet in appearance, softened and could be stirred (a temperature range was noted). Once the sample had melted, the test tube was transferred to a second beaker containing cold tap water (15° C.). The temperature probe was used to record the temperature as the sample was cooled and to probe the sample surface to determine whether the sample had begun to gel. The gel temperature was the temperature upon cooling where the sample no longer flowed to fill in an indentation made by the probe.

The hot sample was then cast, using a draw down bar with a gap set to give a clearance of 3 mm, onto 177 mm by 177 mm by 5 mm metal plates which were pre-sprayed with PAM (lecithin) to facilitate easy removal of film material. The gel coated plates were covered to avoid loss of moisture from the cast film. Cast films were typically refrigerated (less than 8° C.) for at least one-half hour prior to removal of the film for testing. Refrigeration is not required for film formation. Dried film strips were prepared by drying the coated plates in a 40° C. forced air/fan oven. Films dried 2 hours at 40° C. gave an intermediate solids of about 60%, while films dried overnight at 40° C. gave solids of 80% or higher. Test properties were measured at room temperature (approximately 20° C.) unless otherwise specified. The percent of solids of the dried film was determined between the cast film at its formulated solids level and the dried film by difference in weight. Break force (BF) was measured on the cast and dried film strips using a Texture Analyzer TA-108S Mini Film Test Rig.

Unless otherwise indicated, Maltrin M100 was obtained from Grain Processing Corporation, Pure-Cote B760 was obtained from Grain Processing Corporation, Sorbitol Special was obtained from SPI Polyols and Glycerin was obtained from VWR (EP/USP grade).

Example 1

As set forth below, Cgn A was obtained as an alkali processed, clarified extract of *Gigartina skottsbergii*, essentially haploid (gametophyte) plants and recovered by precipitation with alcohol. Minor levels (under 5% total) of lambda- and theta-carrageenans from diploid (tetrasporophyte) plants were also present.

Cgn B was obtained by dissolving Cgn A in water, and recovered by alcohol precipitation and drying. Samples of different molecular weights were obtained by reaction of the dissolved carrageenan with an oxidizing agent to yield Cgn C-F. Sodium hydroxide was added to samples Cgn C-E after the oxidation step and prior to alcohol precipitation to control the pH of the resulting product. The properties of the kappa-2 carrageenans are shown in Table 1. Viscosity of an aqueous solution at 1.5 wt % solids was measured at 75° C. using a Brookfield LVF viscometer at appropriate speeds and spindles. The properties of 2% water gels prepared using 2 wt % of samples Cgn A-F (#1) without added cations, (#2) with 0.2 wt % added KCl and (#3) with 0.2% added KCl and 0.2% CaCl$_2$, respectively, were characterized using a TXTM Texture Analyzer. Gels were tested at 25° C. and the break force (in grams) and the penetration (in centimeters) was recorded.

Cgns A-F below are examples of the kappa-2 carrageenans that can be used in the present invention.

TABLE 1

Properties of Kappa-2 Carrageenans A-F

| Test | Cgn A | Cgn B | Cgn C | Cgn D | Cgn E | Cgn F |
|---|---|---|---|---|---|---|
| Oxidization Treatment | No | No | Yes | Yes | Yes | Yes |
| Mg, % | 0.11 | 0.34 | 0.19 | 0.19 | 0.19 | 0.19 |
| Ca, % | 0.34 | 0.29 | 0.34 | 0.39 | 0.52 | 0.40 |
| K, % | 12.9 | 8.46 | 8.59 | 8.87 | 8.74 | 8.95 |
| Na, % | 0.22 | 0.42 | 0.51 | 0.57 | 0.65 | 0.38 |
| Visc, mPs* | 175 | 144 | 48 | 24 | 14 | 11 |
| PH | 9.4 | 9.42 | 8.93 | 9.03 | 9.16 | 6.7 |

TABLE 1-continued

Properties of Kappa-2 Carrageenans A-F

| Test | Cgn A | Cgn B | Cgn C | Cgn D | Cgn E | Cgn F |
|---|---|---|---|---|---|---|
| 2% water gel | | | | | | |
| BF(g) | 211 | 38 | 21 | 18 | 11 | 12 |
| Penetration (cm) | 7.4 | 13.9 | 11.5 | 9.0 | 7.8 | 16.1 |
| 2% water gel (KCl) | | | | | | |
| BF(g) | 308 | 162 | 126 | 107 | 70 | 51 |
| Penetration (cm) | 7.4 | 9.9 | 7.8 | 7.6 | 7.3 | 6.1 |
| 2% water gel (KCl + CaCl$_2$) | | | | | | |
| BF(g) | 487 | 349 | 514 | 445 | 356 | 158 |
| Penetration (cm) | 3.6 | 3.1 | 6.4 | 5.3 | 5.0 | 1.7 |

*Viscosity measured in 1.5% solids in deionized water at 75° C.

In Table II below, Cgns D and E were formulated as shown and cast as films. The formulations and film properties are reported in Table II. All formulations are considered to be within the scope of the present invention, though some may be more preferable for a particular use than another.

TABLE II

Kappa-2 Carrageenan Formulations and Film Properties

| | Ex 1-1 | Ex 1-2 | Ex 1-3 | Ex 1-4 |
|---|---|---|---|---|
| Ingredients(g) | | | | |
| Water | 834.7 | 834.7 | 666 | 497.4 |
| Cgn D | 0 | 75 | 75 | 75 |
| Cgn E | 75 | 0 | 0 | 0 |
| M-100 | 227.3 | 227.3 | 292.3 | 357.2 |
| Sorbitol SP | 272.2 | 272.2 | 349.9 | 427.7 |
| Glycerin | 90.8 | 90.8 | 116.8 | 142.7 |
| Temp, ° C.* | 81.1 | 82 | 85 | 92 |
| Viscosity, mPas* | 4000 | 13,700 | 22,350 | >50,000 |
| Solids (est) | 40.1% | 40.1% | 50.1% | 60.0 |
| Gel, ° C. | 55-57 | 54-55 | 62 | 77-78 |
| Melt, ° C. | 73-75 | 77-80 | 85 | 90-92 |
| As cast film | | | | |
| BF (g) | 312 | 318 | 404 | 476 |
| Dried film (estimated 80% solids) (16 hours @ 40° C. | | | | |
| Avg film thickness (mm) | 1.5 | 1.0 | 0.87 | 1.1 |
| BF (g) | 5755 | 5220 | 5613 | 3218 |

*Temperature and viscosity of the molten mass prior to casting

All the above formulations showed sufficient dry film strength for use in soft capsule manufacture, though some showed greater strengths than others.

The above Table shows that in Example 1-2 and Example 1-1, the viscosity of the molten mass at processing temperature (13,700 mPas and 4000 mPas, respectively) was controlled by decreasing the molecular weight of Cgn D to Cgn E (expressed as viscosity of 24 mPas and 14 mPas, respectively) with an insignificant impact on film properties.

The melt temperature of the cast material increased (Examples 1-2, 1-3 and -4) as the solids content was increased for a given formulation. In Examples 1-2, 1-3 and 1-4, the gel temperature increased with increasing solids until the gel temperature approached the temperature of the molten mass. Gelation, prior to casting, as indicated by the decreased gel strength of the cast film and the high molten state viscosity (>50,000 mPa) in Example 1-4, is due to the gel temperature approaching the temperature of the molten mass. This indicates the desirability of maintaining the temperature of the molten mass above the gelling temperature during processing if stronger films are desired. Agitation below the gel temperature results in a broken gel structure and decreased strength. Process equipment suitable for use adequately hydrate, homogeneously mix, and easily transport the molten mass for further processing "as is" or to additional operations, such as shaping or film casting.

Example 2

Kappa-2 carrageenan was obtained as an alkali processed, clarified extract of a mixture of *Gigartina skottsbergii* and *Sarcothalia crispata*, primarily haploid (gametophyte) plants. About 10-20% (total) of lambda- and theta-carrageenans from diploid (tetrasporophyte) plants was also present. The extract was recovered and subsequently ion exchanged to provide a kappa-2 carrageenan with low divalency. Properties of the low divalent cation kappa-2 carrageenans (Cgn G-J) are shown in Table III. Cgns G-J are considered to be within the scope of the invention.

TABLE III

Properties of Low Divalent Cation Kappa-2 Carrageenans

|  | Cgn G | Cgn H | Cgn I | Cgn J |
|---|---|---|---|---|
| Cation Exchange | Yes | Yes | Yes | Yes |
| Mg, % | 0.07 | 0.02 | 0.03 | 0.05 |
| Ca, % | 0.06 | 0.01 | 0.16 | 0.15 |
| K, % | 2.19 | 1.00 | 0.00 | 0.67 |
| Na, % | 5.12 | 7.70 | 6.90 | 7.40 |
| Visc, mPs | 6 | 18 | 45 | 98 |
| Visc, mPs* |  | 9 | 20 | 41 |
| PH 2% water gel | 8.12 | 8.7 | 9.6 | 10.1 |
| BF (g) 2% water gel (KCl) | 0 | 0 | 0 | 0 |
| BF (g) 2% water gel (KCl + CaCl$_2$) | 0 | 13 | 29 | 38 |
| BF (g) | 30 | 93 | 112 | 181 |

*Carrageenans H, I and J were measured at 75° C. in a 1.5% kappa-2 carrageenan solids 0.10 molar sodium chloride solution.

Film compositions using the low divalent cation content kappa-2 carrageenans of samples Cgn G-J and the corresponding film properties are presented in Table IV. All formulations below are considered to be within the scope of the present invention, though some may be more preferable for a particular use than another.

TABLE IV

Films Using Low Divalent Cation Kappa-2 Carrageenan

|  | Ex 2-1 | Ex 2-2 | Ex 2-3 | Ex 2-4 |
|---|---|---|---|---|
| Ingredients (g) |  |  |  |  |
| Water | 834.7 | 834.7 | 834.7 | 834.7 |
| Cgn J | 75 | 0 | 75 | 75 |
| Cgn I | 0 | 75 | 0 | 0 |
| KCl | 0 | 0 | 9.0 | 9.0 |
| Starch B790 | 0 | 0 | 0 | 227.3 |
| M-100 | 227.3 | 227.3 | 227.3 | 0 |
| Sorbitol SP | 274.9 | 274.9 | 274.9 | 274.9 |
| Glycerin | 91.7 | 91.7 | 91.7 | 91.7 |
| Temp, ° C.* | 89 | 87 | 87 | 87 |
| Viscosity, mPas* | 5800 | 5800 | 6250 | 10,300 |
| Solids (estimated) | 40% | 40% | 41% | 40% |
| Melt, ° C. | 45-48 | 43 | 66-71 | 70 |
| Gel, ° C. | 35 | 31 | 52 | 48 |
| As Cast Film |  |  |  |  |
| BF (g) | <40 | <40 | 281 | 237 |
| Dried film Solids, (estimated. ~80%) |  |  |  |  |
| Avg film thickness (mm) | — | — | 0.97 | 0.88 |
| BF (g) | 3468 | 3697 | 3236 | 7603 |

*Temperature and viscosity of the molten mass prior to casting

All the above formulations showed sufficient dry film strength for use in soft capsule manufacture, though some showed greater strengths than others.

The ion exchanged kappa-2 carrageenans (I and J) combined with polyols and maltodextrin (as a bulking agent) provided a relatively weaker cast gel film with negligible break force at 40% solids. This is believed to be due to insufficient amounts of potassium cations that are desired to more fully promote carrageenan double helix formation (i.e., gelling) at temperatures that allow the carrageenan to be the primary structuring agent. Examples 2-1 and 2-2 are gel films having relatively lower melt and gel temperatures. Even though gelation potential is not maximized (due to lower potassium levels), Examples 2-1 and 2-2 show a break force of 3468 and 3697, respectively. Example 2-3 demonstrates the effect of potassium ion addition to the structure formed by the kappa-2 carrageenan in Cgn J. Cast strength, although soft, provided sufficient strength for film removal from the casting plate. Structure development by Cgn J, with the addition of potassium ions, is confirmed by the increase in melt and gel temperatures in Example 2-3 as compared to Example 2-1. Break force of the dried film remained comparable to Examples 2-1 and 2-2.

Example 2-4 demonstrates the effect of replacing maltodextrin in Example 2-3 by a modified starch (B790). While viscosity was increased, the gel and melt temperatures remained relatively similar to Example 2-3 which contained the maltodextrin. The cast film strength of Example 2-4 was also relatively equal to Example 2-3. The dried film strength of Example 2-4 was more than doubled as compared to Example 2-3. This clearly indicates the structural synergy between the starch and kappa-2 carrageenan, when both are present with potassium cations (i.e., gelling ions for kappa-2 carrageenan). Potassium ions may be provided by direct addition of inorganic salts, organic salts, or combinations thereof or contained within additional ingredients. Use of kappa-2 carrageenan containing residual processing salts can promote the desired gel formation conditions that maximize gel structure and starch synergy. A homogeneous kappa-2 carrageenan/starch gel structure was formed by casting the molten mass at sufficiently high temperatures to prevent pre-gelation.

Additional formulations of the present invention are provided immediately below.

TABLE V

Kappa-2 Carrageenan Films

|  | Ex 2-5 | Ex 2-6 | Ex 2-7 |
|---|---|---|---|
| Ingredients (g) | | | |
| Water | 834.7 | 834.7 | 825 |
| Cgn H | 61.4 | 0 | 0 |
| Cgn G | 0 | 0 | 90 |
| Cgn I | 0 | 75.0 | 0 |
| Calcium sulfate dihydrate | 1.7 | 0 | 0 |
| Potassium chloride | 0 | 15.0 | 0 |
| Starch B760 | 0 | 0 | 225 |
| M-100 | 227.3 | 227.3 | 0 |
| Sorbitol SP | 275.4 | 272.2 | 272.2 |
| Glycerin | 91.9 | 90.8 | 90.8 |
| Temp, ° C.* | 82 | 88 | 75 |
| Viscosity, mPas* | 6,500 | 16,150 | 18,250 |
| Solids, estimated | 39 | 42 | 40 |
| Melt, ° C. | 74-77 | 85 | 62-65 |
| Gel, ° C. | 56 | 60-65 | 42 |
| PH | 5.8 | 6.9 | 6.9 |
| As Cast Film | | | |
| BF (g) at ~40% Dried 2 hrs @ 40 C. | 338 | 302 | 117 |
| BF (g) at ~60% Dried overnight 16 hours @ 40° C. | 766 | NT | 536 |
| Avg film thickness (mm) | — | 0.62 | |
| BF (g) at ~80% | 3227 | 4470 | 6073 |

NT = not tested
*Temperature and viscosity of the molten mass prior to casting

All the above formulations showed sufficient dry film strength for use in soft capsule manufacture, though some showed greater strengths than others.

Example 2-5 was prepared to have equivalent cation content with example 1-1. Both samples show the same gel melt properties. The higher molecular weight of Cgn E (14 cps) in Example 1-1 provided more structural support to the gel film as compared to Cgn H (6 cps) in Example 2-5, as is shown by the higher break force of the dried film. The higher dried film strength of the Example 2-7 shows that use of modified starch in combination with controlled/reduced molecular weight kappa-2 carrageenan provides overall film structure and indicates complexation of kappa-2 carrageenan with the starch.

Example 3

Table VI presents film formulations and properties of films containing kappa-2 carrageenans blended with alginates. KAHG is a potassium alginate from Laminaria hyperborean having a high level of guluronic (G) units. KAHG had a viscosity of 5 cPs measured in a 1% aqueous solution at 25° C. and an ionic content of 15.73% potassium, 0.63% sodium, 0.07% magnesium and no calcium. Protanal® ester BV4830 is a propylene glycol alginate available from FMC BioPolymer (Philadelphia, Pa.).

TABLE VI

Kappa-2 Carrageenan and Alginate Blends

|  | Ex 3-1 | Ex 3-2 |
|---|---|---|
| Ingredient | | |
| Water | 55.6% | 55.6% |
| Cgn G | | |
| CGN C | 2.7% | 3.6% |
| KAHG | 2.1% | |
| BV4830 | 1.2% | 2.4% |
| Starch B760 | | |
| M-100 | 15.0% | 15.0% |
| Sorbitol SP | 18.0% | 18.0% |
| Glycerin | 6.0% | 6.0% |
| Temp, ° C.* | 87 | 84 |
| Viscosity, mPas* | 4250 | 1050 |
| Solids | 40 | 37 |
| Melt, ° C. | 77-78 | 74-79 |
| Gel, ° C. | 54 | 52 |
| PH | 4.8 | 5.5 |
| Cast film (estimated 40%) | | |
| BF (g) | 142 | 168 |
| Dried film (estimated 80%) | | |
| Avg film thickness (mm) | 0.62 | 0.48 |
| Ingredient | | |
| BF (g) | 3409 | 4004 |

*Temperature and viscosity of molten mass prior to casting

All the above formulations showed sufficient dry film strength for use in soft capsule manufacture, though some showed greater strengths than others.

In example 3-1, potassium ion was supplied by the potassium alginate. Example 3-2 shows that propylene glycol alginate adds to strength to the kappa-2 carrageenan and lowers the processing viscosity.

Example 4

Table VII presents film produced using blends of Kappa-2 carrageenan with Edicol ULV 50, a low viscosity guar from Indian Gum Industries.

Cgn K was a kappa-2 carrageenan obtained as an alkali processed, clarified extract of *Gigartina skottsbergii*, essentially haploid (gametophyte) plants. Minor levels (under 5% total) of lambda- and theta-carrageenans from diploid (tetrasporophyte) plants were also present. Cgn K has a low divalent cation content and low potassium cation content as shown in Table I.

Cgn L was a kappa-2 carrageenan obtained as an alkali processed, clarified extract of a mixture of *Gigartina skottsbergii* and *Sarcothalia crispata*, primarily haploid (gametophyte) plants. About 10-20% (total) of lambda- and theta-carrageenans from diploid (tetrasporophyte) plants were also present. The properties of Cgn K and L are as follows.

TABLE VII

Properties of Kappa-2 Carrageenan

|  | Cgn K | Cgn L |
|---|---|---|
| Cation Exchange | Yes | No |
| Mg, % | 0.05 | 0.05 |
| Ca, % | 0.15 | 0.45 |
| K, % | 0.67 | 13.40 |

TABLE VII-continued

Properties of Kappa-2 Carrageenan

|  | Cgn K | Cgn L |
|---|---|---|
| Na, % | 7.40 | 0.90 |
| Visc, mPs | 98 | NT |
| PH | 10.1 | NT |
| 2% water gel |  |  |
| BF (g) 2% water gel (KCl) | 0 | " |
| BF (g) 2% water gel (KCl + CaCl2) | 38 | " |
| BF (g) | 181 | " |

Table VIII shows the compositions and the film properties for formulations prepared using low viscosity guar gum in combination with kappa-2 carrageenans.

TABLE VIII

Formulations and Films Using Guar with Kappa-2 Carrageenan

|  | Ex 4-1 | Ex 4-2 | Ex 4-3 | Ex 4-4 |
|---|---|---|---|---|
| Ingredients(g) |  |  |  |  |
| Water | 836.3 | 836.3 | 836.3 | 836.3 |
| Cgn L | 40.5 | 20.3 | 0.0 | 0.0 |
| Cgn K | 0.0 | 20.3 | 40.5 | 40.5 |
| GUAR ULV 50 | 49.5 | 49.5 | 49.5 | 49.5 |
| Starch B760 | 220.8 | 220.8 | 220.8 | 220.8 |
| PotassiumChloride | 0.0 | 0.0 | 4.5 | 4.5 |
| Sorbitol SP | 264.4 | 264.4 | 264.4 | 264.4 |
| Glycerin | 88.2 | 88.2 | 88.2 | 88.2 |
| Total weight (g) | 1500.0 | 1500.0 | 1500.0 | 1500.0 |
| Temp, ° C.* | 90 | 90 | 87 | 95 |
| Viscosity, mPa · s* | >50,000 | >50,000 | >50,000 | >50,000 |
| As cast |  |  |  |  |
| Gel, ° C. | 68-69 | 69 | 50 | 54-65 |
| Melt, ° C. | 85-87 | 86-88 | 67-68 | 76-83 |
| PH | 5.8 | 5.9 | 5.2 | 5.2 |
| Cast film |  |  |  |  |
| Solids, est | 45% | 42% | 40.2% | 45% |
| BF (g) | 239 | 349 | 130 | 330 |
| Dried film (2 hr 40° C.) |  |  |  |  |
| Solids, est | 60% | 60% | 63% | 66% |
| BF (g) | 953 | 2189 | 1194 | 1631 |
| Dried film (16 hr, 40° C.) |  |  |  |  |
| Solids, est | 87% | 75% | 84% | 84% |
| BF (g) | 7476 | 6901 | 6276 | 8733 |

*Temperature and viscosity of the molten mass prior to casting.

All of the above formulations of the present invention showed sufficient dry film strength for use in soft capsule manufacture, though some showed greater strength than others.

Example 5

The following examples show films made using the fluid mixing apparatus of FIG. 3. In these examples, Part A and Part B were pumped from separate holding tanks at ambient temperature, as two separate streams 4, 6, into two different inlet ports 42, 44 which fed the steam injection fluid mixing apparatus device 10. The two individual streams 4, 6 were combined at the interface of the steam in the mixing zone 52 of the fluid mixing apparatus 10. The separate solutions of Part A and Part B were readily pumped into the fluid mixing apparatus 10 and mixed with steam 2. The steam 2 was introduced to the mixing zone at a pressure of 120 psi. The resulting molten mass or slurry mixture 8 flowed out of the exit port 56 of the fluid mixing apparatus 10. The mixture 8 was poured onto a smooth surface and drawn down to form a homogeneous film 9.

To measure the viscosity of the mixture 8, approximately 500 ml sample of the mixture 8 was collected from the outlet 56 and poured into a jar. The temperature, pH and viscosity were measured for this sample at 95° C. A Brookfield LVF viscometer was used to measure the viscosity. An appropriate speed and spindle combination were used such that a reading could be taken. The dial reading was converted to dynamic viscosity (cP).

To measure the film strength and solids level, the molten mass 8 was collected from the outlet 56 then cast using a draw down bar, with a gap set at 3 mm, onto a stainless steel metal plate. The initial films 9 or "fresh films" were collected. Portions of the fresh films 9 were dried by placing them in a 40° C. forced air oven. Break force was measured on the fresh and dried film strips using a Texture Analyzer TA-108S Mini Film Test Rig. The percent solids were determined by measuring the difference between the initial weight of the fresh film and the final weight of the dried films.

To measure the gel temperature, a portion of the molten mass 8 was collected from the outlet 56 of the mixing apparatus 10 and transferred to a test tube. Half of the test tube remained empty. A glass thermometer was inserted into the molten mass 8. The material 8 was allowed to cool under room temperature conditions. After each degree of cooling, the thermometer was removed from the material 8. When a small, temporary indentation was observed in the surface of the mass 8, this temperature was recorded. The thermometer was re-inserted into the mass 8, which was allowed to cool further. The thermometer was removed and re-inserted at every degree of cooling until such a time as a permanent indentation formed in the mass 8, such that the indentation did not refill. The temperature at which the permanent indentation formed was recorded. The gel temperature reported was the range between the two recorded temperatures.

TABLE IX

Mixtures Containing Kappa-2 Carrageenan

| Example No. | 5-1 | 5-2 | 5-3 |
|---|---|---|---|
| Part A (%) |  |  |  |
| Kappa-2 Carrageenan A | 7.0 | 8.4 | 8.9 |
| Glycerin | 26.5 | 31.8 | 33.5 |
| Part B (%) |  |  |  |
| Starch | 16.4 | 19.7 | 20.7 |
| Water | 50.0 | 40.0 | 36.9 |
| Mixing chamber temp. (° C.) | 107 | 107 | 108 |
| Outlet temp (° C.) | 101 | 102 | 102 |
| Viscosity cP (@ 95° C.) | 7300 | 5200 | 48000 |
| PH | 7.3 | not tested | 8 |
| % solids | 53 | 54 | 65 |
| Gel temp. (° C.) | 46-50 | 43-47 | 53-60 |
| wet film strength (grams) | 267 | 214 | 983 |
| dry film strength (grams) | 2958 | 6798 | 4594 |
| Avg film thickness (mm) (% solids) |  |  | 1.3(74%) 1.7(59%) |

All the above formulations showed sufficient dry film strength for use in soft capsule manufacture, though some showed greater strengths than others.

TABLE X

Mixtures Containing Kappa-2 Carrageenan and PGA

| Example No. | 5-4 | 5-5 | 5-6 | 5-7 |
|---|---|---|---|---|
| Part A (%) | | | | |
| Kappa-2 Carrageenan A | 2.7 | 3.2 | 3.2 | 4.0 |
| PGA | 3.3 | 3.9 | 3.9 | 4.9 |
| Glycerin | 22.4 | 26.5 | 26.5 | 33.5 |
| Part B (%) | | | | |
| KOH | 0.0 | 0.0 | 0.1 | 0.0 |
| $K_2CO_3$ | 0.0 | 0.0 | 0.0 | 0.3 |
| Starch | 13.9 | 16.4 | 16.4 | 20.7 |
| Water | 57.8 | 50.0 | 49.9 | 36.6 |
| Mixing chamber temp. (° C.) | 108 | 107 | 108 | 107 |
| Outlet temp (° C.) | 102 | 102 | 102 | 101 |
| Viscosity cP (@ 95° C.) | 5500 | 4650 | 2200 | 12400 |
| PH | 4.1 | 4.2 | 8.7 | 6.3 |
| % solids | 48 | 50 | Not tested | 58 |
| Gel temp. (° C.) | 35-40 | Not tested | Not tested | 58-66 |
| wet film strength (grams) | 60 | 117 | Not tested | 337 |
| dry film strength (grams) | 2408 | 3069 | 4335 | 4561 |
| Avg film thickness (mm) (% solids) | | | | 1.2(91%) 1.1(57%) |

All the above formulations showed sufficient dry film strength for use in soft capsule manufacture, though some showed greater strengths than others.

TABLE XI

Mixtures Containing Kappa-2 Carrageenan and LV Guar

| Example No. | 5-8 | 5-9 |
|---|---|---|
| Part A (%) | | |
| Kappa-2 Carrageenan B | 4.0 | 4.2 |
| ULV guar | 4.9 | 5.1 |
| Glycerin | 33.5 | 27.0 |
| Sorbitol | 0.0 | 8.1 |
| Part B (%) | | |
| Starch | 20.7 | 21.8 |
| Water | | |
| Mixing chamber temp. (° C.) | 108 | 108 |
| Outlet temp (° C.) | 102 | 102 |
| Viscosity cP (@ 95° C.) | 7800 | 69000 |
| PH | 5.6 | 5.5 |
| % solids | 57 | 55 |
| Gel temp. (° C.) | >100 | >100 |
| Wet film strength (grams) | 3402 | 921 |
| Dry film strength (grams) | 6587 | 9234 |

All the above formulations showed sufficient dry film strength for use in soft capsule manufacture, though some showed greater strengths than others.

The following Tables XII and XIII provide descriptions of the components specified in this example.

TABLE XII

Component Descriptions

| Name | Trade Name | Supplier | Description |
|---|---|---|---|
| Propylene glycol alginate (PGA) | Protanal BV 4830 | FMC Corporation | |
| low viscosity guar (LV guar) | Edicol ULV 50 | Indian Gum Industries, Ltd. | |
| Glycerin | | Callahan Chemical | 99.70% |
| Sorbitol | Sorbo | SPI Polyols | 70% sorbitol solution, USP/FCC |
| starch | Pure-Cote B790 | Grain Processing Corporation | |

TABLE XIII

Carrageenan Descriptions

| Reference | Description | Supplier |
|---|---|---|
| Kappa-2 Carrageenan A | An alkali processed, clarified, low divalency extract of a mixture of *Gigartina skottsbergii* and *Sarcothalia crispata*, primarily haploid (gametophyte) plants, such extract being commonly known as "kappa-2 carrageenan". Includes about 10-20% (total) of lambda and theta-carrageenans from diploid (tetrasporophyte) plants. Defined as the natural random block copolymer of kappa- and iota-carrageenan in the ratio of about 1.0 to 3.0:1 respectively, and has significantly different functionalities compared to mixing individual kappa and iota-carrageenan natural polymers at the same ratio. | FMC Corporation |
| Kappa-2 Carrageenan B | An alkali processed, clarified, low divalency extract of *Gigartina skottsbergii*, essentially haploid (gametophyte) plants, such extract being commonly known as "kappa-2 carrageenan". Also includes minor levels (under 5% total) of lambda- and theta-carrageenans from diploid (tetrasporophyte) plants. Defined as the natural random block copolymer of kappa- and iota-carrageenans in the ratio of about 1.0 to 3.0:1 respectively, and has significantly different functionalities compared to mixing individual kappa- and iota-carrageenan natural polymers at the same ratio. | FMC Corporation |

As described and demonstrated above, the films made in accordance with this invention can be used in conventional capsule making equipment previously used for making gelatin capsules. The hydrocolloid films produced by the present invention produce less waste and provide for easier processing than gelatin-based films.

Example 6

Kappa-2 carrageenan was obtained as an alkali processed, clarified extract from *Gigartina skottsbergii* and *Sarcothalia crispata*, respectively, using primarily haploid (gametophyte) plants. The total of lambda- and theta-carrageenans from diploid (tetrasporophyte) plants was about 0 to 5% for the *Gigartina skottsbergii* compared to about 5 to 10% for the *Sarcothalia crispata*. The extract was recovered and subsequently ion exchanged to provide kappa-2 carrageenans with low divalency. Properties of the kappa-2 carrageenans are shown in Table (XIV) and are considered to be within the scope of the invention.

TABLE XIV

Properties of Sodium and Potassium Kappa-2 Carrageenans

| Seaweed source | Cgn Na K2-S *Gigartina skottsbergii* | Cgn K K2-S *Gigartina skottsbergii* | Cgn Na K2-N *Sarcothalia crispata* | Cgn K K2-N *Sarcothalia crispata* |
|---|---|---|---|---|
| Mg % | 0.00 | 0.12 | 0.03 | 0.12 |
| Ca % | 0.04 | 0.34 | 0.11 | 0.43 |
| K % | 1.24 | 9.27 | 1.35 | 8.63 |
| Na % | 6.53 | 0.68 | 7.23 | 1.34 |
| Visc, mPs | 45.5 | 39.5 | 62.5 | 31.5 |
| pH | 7.46 | 8.51 | 7.1 | 7.91 |
| 2% water gel | | | | |
| BF (g) | incipient | 38 | 17 | 102 |
| Penetration (cm) | 7.46 | 6.9 | 21 | 12.1 |
| 2% water gel (KCl) | | | | |
| BF (g) | 10 | 134 | 30 | 179 |
| Penetration (cm) | 5.7 | 1.9 | 5.0 | 2.7 |
| 2% water gel (KCl + CaCl2) | | | | |
| BF (g) | 112 | 279 | 114 | 263 |
| Penetration (cm) | 2.1 | 2.7 | 2.7 | 2.0 |

K2 = Kappa-2 carrageenan

Film compositions for kappa-2 carrageenans and the corresponding film properties are presented in Table XV. These films were formed using the spreader box technique. The formulations use a 50/50 blend of kappa-2-carrageenans from *Gigartina skottsbergii* and *Sarcothalia crispata* and have varying potassium cation content. All formulations below are considered to be within the scope of the present invention, though some may be more preferable for a particular use than another.

TABLE XV

Films of Kappa-2-Carrageenans of Different Seaweed Source and Cation Content.

| | Ex 1 | Ex 2 | Ex 3 | Ex 4 |
|---|---|---|---|---|
| Ingredients (g) | | | | |
| Na K2-S* | 162.6 | 162.6 | 195.1 | 0.0 |
| Na-K2S-N* | 162.6 | 0.0 | 195.1 | 0.0 |
| K-K2S-S* | 0.0 | 0.0 | 0.0 | 162.6 |
| K-K2-N* | 0.0 | 162.6 | 0.0 | 162.6 |
| Water | 1851.5 | 1851.5 | 1851.5 | 1851.5 |
| Starch B790 | 858.5 | 858.5 | 858.5 | 858.5 |
| Glycerin | 1300.8 | 1300.8 | 1300.8 | 1300.8 |
| As cast film | | | | |
| Gel, ° C. | 35-40 | 63 | 50 | 58 |
| Melt, ° C. | 58-60 | 83-85 | 69 | 93-95 |
| pH | 5.3 | 5.6 | 6.6 | 5.6 |
| Cast film | | | | |
| Solids, est | 57.3% | 57.3% | 57.3% | 57.3% |
| BF, g | 214.3 | 610.5 | 459.1 | 901.4 |
| Penetration, cm | 2.0 | 1.6 | 2.1 | 1.6 |
| Dried film (16 hr, 40° C.) | | | | |
| Solids, est | 95 | 91 | 86 | 93 |
| BF, g | 5132 | 6902 | 8914 | 4517 |
| Penetration, cm | 2.3 | 1.8 | 1.8 | 1.6 |

* = Kappa-2 carrageenan

All the above formulations showed sufficient dry film strength for use in soft capsule manufacture, though some showed greater strengths than others. The sodium form of the kappa-2 carrageenan (Examples-1 and -3) provided the most elasticity, while the all potassium form of kappa-2 carrageenan (Example-4) yielded films that were more rigid though useful. Processing the formulation containing the potassium kappa-2 carrageenann was also difficult in that the mixture started to gel while such was being transferred from the Ross mixer to the film forming machine. The generated films in Example-4 were lower in strength, most likely due to pre-gelation during the transfer and/or film forming process. Excellent temperature control is necessary when it is desired to maximize film strength and avoid quick transition from the molten mass to the rubbery state and then to the glassy state (glass transition temperature). The film using the "mixed cation" kappa-2-carrageenan (Example-2) provided melt and cast film properties intermediate between the films containing the all sodium and all potassium kappa-2 carrageenans, with an elevated gelling temperature and a decrease in elasticity (as shown by penetration) compared to the all sodium kappa-2-carrageenan.

Example 7

Soft Capsule Example

Soft gel capsules (7.5 oval) containing mineral oil (Formula A below) were produced using a Technophar SGM1010 soft capsule machine with 7.25 inch long by 4 inch diameter dies. Preparation of the molten mass used to form the capsule shell was as follows: 11.35 lbs of kappa-2-carrageenan (as defined in Example 5 as Kappa-2 Carrageenan A) was added to a charge of 33.89 lbs of glycerin in a Ross DS40 jacketed vacuum mixer and dispersed at maximum speed for 5 minutes. An additional 11.35 lbs of kappa-2 carrageenan (as defined in Example 5 as Kappa-2 Carrageenan A) was added to the mixture and dispersed an additional 5 minutes. A premix of 50 lbs of PureCote B790 modified starch in 94.1 lbs of deionized water was then charged to the mixer. The mixer hood was closed and a 26 inch vacuum was pulled to remove air. The contents were mixed for 30 minutes with the planetary mixer at maximum speed and the disperser at ⅓ maximum speed. The vacuum was locked in and the contents of the mixer were then mixed while heating to 90° C. by applying low pressure steam (<10 psig) to the mixer jacket. After reaching a temperature of 90° C., the disperser speed was gradually increased to ⅔ maximum while maintaining the molten mass at a temperature of at least 90° C. for 45 minutes. The molten mass was dispensed using a pressurized plate to urge the molten mass to flow as needed from the Ross mixer through a temperature controlled, electrically heated (~125° C.) flexible hose to the covered spreader box. The cast films formed in the spreader box were continuous and even. The films were transported by rollers to the capsule forming dies where capsules were formed, filled with mineral oil and sealed. The capsule sealing temperature was 62° C. and the sealing pressure was ~2 bars. The ability to seal was improved as the thickness of the ribbon was decreased from 0.28 inches to 0.16 inches. Capsules were tunnel dried for 72 hours at 80° F. and 19% RH. The integrity of the capsule seal remained good after drying. The cast film made from this formulation was dark amber and cloudy with a slight seaweed odor. The break force of the film (0.3 mm in thickness) was 310 g at 58% solids. The breakforce of the film after drying overnight at 40° C. and 40% RH (~80% solids) was 3309 g. See A in the Table below.

Additional soft capsules (Formula B below) encapsulating mineral oil were produced according to the above process and equipment using a second formulation comprising 39.7 lbs of Sorbitol SP, 59.5 lbs of glycerin, 19.6 lbs of sodium ion exchanged kappa-2 carrageenan (a 50/50 mixture of carrageenans J and I above), 44.6 Lbs of PureCote B760 starch and 92.6 pounds of water. The Sorbitol SP was added in the starch/water premix. Films produced using this formulation were odorless, transparent and a medium color. The as-cast film had a thickness of 0.6 mm and a break force strength of 263 g at 55% solids. A film sample which was dried overnight at 40° C. and 40% RH (~80% solids) had a thickness of 0.7 mm and a breakforce of 6463 g. The as-cast film was more elastic and stretched when fed over the rollers into the capsule dies. Capsules were formed using a capsule seal temperature of 42° C. and a seal pressure of 0.5 bar. Mineral oil was encapsulated.

The capsules were evaluated for weight, film thickness for each half of the capsule, and burst strength. Burst strength was measured by compressing the capsule to failure. The compression probe had a speed of 1 mm/sec. Ten capsules were tested for each condition. The shell strength is reported as the capsule burst strength with the seam horizontally positioned. The seam strength was measured for 10 capsules with the seam vertically positioned. Results are shown in Table XVI. Both kappa-2-carrageenen films were flexible as indicated by the burst distance and produced a strong capsule seal as indicated by a capsule burst strength that was approximately the same for the capsule shell and the capsule seam and that the capsule did not fail at the seam but at the tip on the seam (away from the point of pressure).

TABLE XVI

Capsule Properties

| Capsule Formula | Capsule Weight, (mg) | Film wt/fill weight (mg) | Thickness film1/film2, mm | Shell burst distance Mm | Shell strength, Newtons | Seam burst distance mm | Seam strength, Newtons |
|---|---|---|---|---|---|---|---|
| FormulaA | 471 | 151/320 | 357/312 | 6.3 | 206 | 6.3 | 210 |
| FormulaB | 499 | 187/312 | 420/370 | 5.3 | 124 | 5.1 | 105 |

Example 8

A kappa-2 carrageenan was produced from *Sarcothalia crispata* having a final composition of approximately 74% unmodified kappa-2 carrageenan and 26% lambda carrageenan. The kappa-2 carrageenan had a viscosity of 340 cps and a pH of 9.4 when tested as a 1.5% aqueous solution at 75° C. The ionic content is approximately 4.4% potassium, 4.0% sodium, 0.2% calcium, and 0.4% magnesium. A composition was prepared by adding 2% of the kappa-2 carrageenan to a mixture of 20% glycerin and 78% deionized water, mixing while heating to 85° C., holding while mixing at 85° C. for 15 minutes, adjusting for any water loss with deionized water @ 85° C., then casting into a Petri dish and drying overnight at 45° C. to a film of about 80% solids. The dried film had a breakforce strength of 469 grams and a penetration of 3.3 cm.

Example 9

The following procedure was used to prepare 2.25% kappa-2 carrageenan samples of varying molecular weight as indicated by viscosity where viscosity was measured at 75° C. for a 1.5% solids aqueous solution: 105 grams of water and 147 grams of corn syrup were mixed in a beaker. A dry premix of kappa-2 carrageenan, granulated sugar and salts (as indicated in Table XVII) was added to the liquid and heated with agitation to 95° C. The hot liquid was poured into 2 gel dishes and 2 test tubes (½ full). The gel dishes and one test tube (positioned to obtain a gel surface at 45 degrees for use in measuring the melt temperature) were placed in a water bath at 10° C. for an hour. The second test tube was used to measure the gel temperature. The as-cast solids were approximately 62%. The gel and melt temperatures for the samples 1b, 2b and 3b which contained added potassium and calcium cations were above 50° C. and relatively constant with increasing molecular weight. The gel and melt temperatures of samples 1a, 2a and 3a which contained ion exchanged kappa-2 carrageenans were all observed to be below 50° C. The gel and melt temperatures were decreased as the molecular weight (as measured by viscosity) was lowered. In particular, sample 1a, which contained the kappa-2 carrageenan with viscosity of 9 mPas, provided a gel film with a decreased gel temperature of 25° C. and a melt temperature of 36° C.

TABLE XVII

Kappa 2 Carrageenan Formulations and Properties

| Ingredient (g) | 1a | 2a | 3a | 1b | 2b | 3b |
|---|---|---|---|---|---|---|
| K2 (9 mPas) Cgn H | 7.88 | 0 | 0 | 7.88 | 0 | 0 |
| K2 (20 mPas) Cgn I | 0 | 7.88 | 0 | 0 | 7.88 | 0 |
| K2 (41 mPas) Cgn J | 0 | 0 | 7.88 | 0 | 0 | 7.88 |
| Sugar | 90.13 | 90.13 | 90.13 | 88.78 | 88.78 | 88.78 |
| CaCl2 | 0 | 0 | 0.0 | 0.58 | 0.58 | 0.58 |
| KCl | 0 | 0 | 0.0 | 0.76 | 0.76 | 0.76 |
| As Cast | | | | | | |
| BF (g) | No break | No break | No break | 819 | 964 | 1178 |
| Penetration, cm | | | | 5.0 | 13.0 | 7.5 |
| Melt temp. ° C. | 36 | 39.5 | 42 | 75 | 76-77 | 77 |
| Gel temp. ° C. | 25 | 35.5 | 34-36 | 57 | 58.5-60 | 58-59 |

K2 = Kappa-2 carrageenan

While the invention has been described in detail and with reference to specific embodiments thereof, it will be apparent to one skilled in the art that various changes and modifications can be made therein without departing from the spirit and scope thereof.

What is claimed is:

1. A homogeneous, thermoreversible gel film comprising a film forming amount of kappa-2 carrageenan, and optionally at least one of a plasticizer, a second film former, a bulking agent, and a pH controlling agent; wherein said film: (i) further comprises sodium cation, (ii) has a solids content of at least 50% based on all components in the gel film, and (iii) has a break force strength of at least 1,500 grams.

2. The film of claim 1, wherein said sodium cation is present in an amount less than 50% by dry weight of the kappa-2 carrageenan in the gel film.

3. The film of claim 1, wherein said kappa-2 carrageenan is present in an amount of at least 0.5% by dry weight of the gel film.

4. The film of claim 1, wherein said kappa-2 carrageenan is present in an amount of 0.5% to 25% by dry weight of the gel film.

5. The film of claim 1, wherein said kappa-2 carrageenan is present in an amount of 1.5% to 25% by dry weight of the gel film.

6. The film of claim 1, wherein said kappa-2 carrageenan is present in an amount of at least 10% of the total dry weight of film formers in the gel film.

7. The film of claim 1, wherein said kappa-2 carrageenan is present in an amount of at least 20% of the total dry weight of film formers in the gel film.

8. The film of claim 1, wherein said kappa-2 carrageenan is present in an amount of at least 50% of the total dry weight of film formers in the gel film.

9. The film of claim 1, wherein said kappa-2 carrageenan is present in an amount of at least 80% of the total dry weight of film formers in the gel film.

10. The film of claim 1, wherein said kappa-2 carrageenan is the only film former present in the gel film.

11. The film of claim 1, wherein said second film former is selected from the group consisting of starch, starch derivative, starch hydrozylate, cellulose gums, kappa carrageenan; iota carrageenan; alginates, propylene glycol alginate, polymannan gums, dextran, pectin, gellan, pullulan, alkylcellulose ethers and modified alkyl cellulose ethers.

12. The film of claim 1, wherein said plasticizer is at least one member selected from the group consisting of glycerin, sorbitol, polydextrose, maltitol, lactitol, and polyalkylene glycols; said second film former is at least one member selected from the group consisting of a starch, starch derivative, starch hydrozylate, cellulose gum, hydrocolloid, an alkylcellulose ether and a modified alkyl cellulose ether; and said bulking agent is at least one member selected from the group consisting of microcrystalline cellulose, microcrystalline starch, starch, starch derivatives, inulin, starch hydrozylates and polydextrose.

13. The film of claim 1, having a break force strength of at least 4,000 grams.

14. The film of claim 1, having a break force strength of at least 5,000 grams.

15. The film of claim 1, having a break force strength of at least 6,000 grams.

16. The film of claim 1 having a solids content of at least 60% by weight of the gel film.

17. The film of claim 1 having a solids content of at least 80% by weight of the gel film.

18. The film of claim 1 having a solids content of at least 90% by weight of the gel film.

19. A process for making the gel films in any one of claim 1-18, comprising the step of:
   (i) heating, hydrating, mixing, solubilizing and, optionally, de-aerating a composition of said kappa-2 carrageenan and sodium cation and optionally at least one of said plasticizer, said second film former, said bulking agent and said pH controlling agent in an apparatus providing sufficient shear, temperature and residence time to form a homogeneous, thermoreversible, molten composition thereof, wherein said temperature is at or above the solubilizing temperature of the molten composition; and
   (ii) cooling said molten composition at or below its gelling temperature to form the gel film, wherein the film has a solids content of at least 50% based on all the components in the gel film and has a break force of at least 1,500 grams.

20. The process of claim 19, wherein said molten composition is fed directly into at least one of a mixer, pump or devolatilizer prior to cooling.

21. The process of claim 19, wherein said apparatus is a Ross mixer, Stephan processor, extruder, jet cooker or fluid mixing apparatus.

22. Soft capsules comprising capsule walls and an encapsulated substance wherein said capsule walls comprise the films of any one of claims 1-18.

23. The soft capsules of claim 22, wherein said encapsulated substance is at least one member selected from the group consisting of pharmaceuticals, vitamins, nutritional supplements, paint, paintballs, pigments, agriculturals, cosmetics, antioxidants, flavorant or food.

24. A solid form comprising a fill material encapsulated by the homogeneous, thermoreversible gel film of any one of claims 1-18.

25. The solid form of claim 24, wherein said fill material is a powder, tablet, caplet, microcapsule or capsule.

26. The solid form of claim 24, wherein said solid form is a hard capsule.

27. The film of claim 1, comprising 0.5 to 25 wt % kappa-2 carrageenan, 10 to 50 wt % second film former, 5 to 40 wt % plasticizer, and a solids content of 50 to 90%, all by weight of the gel film, and optionally, a pH control agent.

28. A soft capsule comprising the film of claim 27 encapsulating a fill material.

29. The film of claim 1 wherein said kappa-2 carrageenan has a viscosity of less than 10 cps at 75° C. in a 1.5% kappa-2 carrageenan solids 0.10 molar sodium chloride solution.

30. A soft capsule comprising the film of claim 29 encapsulating a fill material.

31. The gel film of claim 1 further comprising a flavorant.

32. A soft capsule comprising the film of claim 31 encapsulating a fill material.

33. The gel film of claim 31, wherein said flavorant is sugar.

34. The film of claim 1, wherein said film does not contain a plasticizer.

35. The film of claim 1 consisting of said kappa-2 carrageenan, flavorant, sodium cation, and water.

36. The film of claim 35, wherein said flavorant is corn syrup.

37. A soft capsule comprising the film of claim 35 encapsulating a fill material.

38. The film of claim 1 further comprising at least one cation selected from the group consisting of calcium, magnesium, aluminum and chromium, wherein said at least one cation is present in an amount less than 5% by dry weight of the kappa-2 carrageenan in the film.

39. The film of claim 38, wherein said at least one cation is present in an amount less than 1% by dry weight of the kappa-2 carrageenan in the film.

40. A soft capsule comprising the film of claim 38 encapsulating a fill material.

41. The film of claim 27 further comprising at least one cation selected from the group consisting of calcium, magnesium, aluminum and chromium, wherein said at least one cation is present in an amount less than 5% by dry weight of the kappa-2 carrageenan in the film.

42. A soft capsule comprising the film of claim 41 encapsulating a fill material.

* * * * *